(12) United States Patent
Abouabdellah et al.

(10) Patent No.: US 8,034,818 B2
(45) Date of Patent: Oct. 11, 2011

(54) THERAPEUTIC USES OF DERIVATIVES OF PIPERIDINYL- AND PIPERAZINYL-ALKYL CARBAMATES

(75) Inventors: Ahmed Abouabdellah, Thiais (FR); Philippe Burnier, Maisons-Laffitte (FR); Christian Hoornaert, Antony (FR); Jean Jeunesse, Paris (FR); Frederic Puech, La Celle Saint-Cloud (FR)

(73) Assignee: Sanofi-Aventis, Paris (FR)

( * ) Notice: Subject to any disclaimer, the term of this patent is extended or adjusted under 35 U.S.C. 154(b) by 1203 days.

(21) Appl. No.: 11/670,690

(22) Filed: Feb. 2, 2007

(65) Prior Publication Data

US 2007/0142350 A1 Jun. 21, 2007

Related U.S. Application Data

(60) Division of application No. 11/262,211, filed on Oct. 28, 2005, now Pat. No. 7,214,798, which is a continuation of application No. PCT/FR2004/001102, filed on May 6, 2004.

(51) Int. Cl.
*A61K 31/4965* (2006.01)
*C07D 217/22* (2006.01)

(52) U.S. Cl. .................... 514/255.03; 546/143
(58) Field of Classification Search ............. 514/255.03; 544/393
See application file for complete search history.

(56) References Cited

U.S. PATENT DOCUMENTS

| 4,539,323 | A | * | 9/1985 | Mentrup et al. | ......... | 514/266.22 |
|---|---|---|---|---|---|---|
| 6,995,184 | B2 | | 2/2006 | Barth et al. | | |

FOREIGN PATENT DOCUMENTS

| WO | WO 98/43636 | 10/1998 |
|---|---|---|
| WO | WO 01/64632 | 9/2001 |

OTHER PUBLICATIONS

Beringue, V., et. al., Creutzfeldt-Jakob disease: Therapeutic Strategies, Expert Opinion on Investigational Drugs (1997), vol. 6, No. 4, pp. 345-348 ( CA 126:324757).
Brittan, H.G., et. al., Polymorhphism in Pharmaceutical Solids, Pharmaceutical Sciences vol. 95 pp. 5-8, (1999).
Cecil, et. al., Disorders of the Inflammatory Response, Textbook of Medicine (1982), pp. 1397-1401.
Grever, M. R., et. al., The National Cancer Instituted: Cancer Drug Discovery and Development Program, Seminars in Oncology, vol. 19, No. 6 (1992) pp. 622-638.
Heinonen, T.M., et. al., Inhibition of Acyl Coenzyme A-Cholesterol Acyltransferase: A Possible Treatment of Atherosclerosis?, Current Atherosclerosis Reports (2002) vol. 4, No. 1, Summary.
Thomas, D., et. al., Is Regression Possible of Atherosclerosis Possible?, Archives de Maladies du Coeur et des Vaisseaux, (1992), vol. 85, No. III, Summary.
Tomlinson, D.R., et. al., Neurotrophic Factors—Regulation of Neuronal Phenotype, Neuroscience Research Communication (1997) vol. 21, No. 1, pp. 57-66 (CA 127:174580).
Ueda, et al.; "The fatty acid amide hydrolose (FAAH)"; Chemistry and Physics of Lipids (2000), 108, pp. 107-121.
Martin, et al.; "Cannabinoid Transmission and Pain Reception", Neurobiology of Disease, 1998, 5, pp. 447-461.
Pionnelli, et al.; The Endocannabinoid System as a Target for Therapeutic Drugs; Trends in Pharmacological Sciences 2000, 21, pp. 218-224.
Van Sickle, et al.; "Cannabinoids Inhibit Emesis Through CB1 Receptors in the Brainstorm of the Ferret"; Gastroenterology 2001, 121, pp. 767-774.
Porter, et al; "The Endocannabinoid Nervous System; Unique Opportunities for Therapeutic Intervention"; Pharmacology and Therapetuics 2001, 90, pp. 45-60.
Carley, et al.; "Functional Role for Cannabinoids in Respiratory Stability During Sleep", Neuropsychopharmacology 2001, 25, pp. S36-S39.
Smith, et al.; "Anandamide Induces Cardiovascular and Respiratory Reflexes via Vasosensory Nerves in the Anasthetized Rat"; British Journal of Pharmacology 2001, 134, pp. 655-663.
Consroe; "Brain Cannabinoid Systems as Targets for the Therapy of Neurological Disorders"; Neurobiology of Disease 1998, 5, pp. 534-551.
Salzet, et al.; "Comparative biology of the Endocannabinoid System"; European Journal of Biochemistry 2000, 267, pp. 4917-4927.
Petrocellis, et al.; "Endocannabinoids and Fatty Acid Amides in Cancer, Inflammation and Related Disorders"; Chemistry and Physics of Lipids 2000, 108, pp. 191-209.
Jaggar, et al.; "The Anti-Hyperalgesic Actions of the Cannabinoid Anandamide and the Putative CB2 Receptor Agonist Palmitoyethanolamide in Visceral and Somatic Inflammatory Pain"; Pain 1998, 76, pp. 189-199.
Alzzo, et al., "The Gastrointestinal Pharmacology of Cannabinoids"; Current Opinion in Pharmcology 2001, 1, pp. 597-603.
Mendelson, et al., "The Hypnotic Actions of the Fatty Acid Amide, Oleamide"; Neuropsychopharmacology 2001, 25, pp. S36-S39.

* cited by examiner

*Primary Examiner* — Noble Jarrell
*Assistant Examiner* — Erich A Leeser
(74) *Attorney, Agent, or Firm* — Serena Farquharson-Torres; Scully, Scott, Murphy & Presser, P.C.

(57) ABSTRACT

Therapeutic uses of a compound corresponding to the general formula (I):

(I)

in which A=N or $CR_2$; $R_2$=H, F, OH, CN, $CF_3$, $C_{1-6}$-alkyl, $C_{1-6}$-alkoxy; n=2 or 3 and m=2 when A=N; n=1, 2 or 3 and m=1 or 2 when A=$CR_2$; B=covalent bond or $C_{1-8}$-alkylene; $R_1$=optionally substituted heteroaryl; $R_3$=$CHR_4CONHR_5$; $R_4$=H or $C_{1-6}$-alkyl; $R_5$=H, $C_{1-6}$-alkyl, $C_{3-7}$-cycloalkyl, $C_{3-7}$-cycloalkyl-$C_1$-$C_6$-alkylene;
in the form of a base, an acid-addition salt, a hydrate or a solvate.

6 Claims, No Drawings

THERAPEUTIC USES OF DERIVATIVES OF PIPERIDINYL- AND PIPERAZINYL-ALKYL CARBAMATES

BACKGROUND OF THE INVENTION

The invention relates to piperidyl- and piperazinyl-alkyl-carbamate derivatives and to the preparation and therapeutic application thereof.

SUMMARY OF THE INVENTION

The compounds of the invention correspond to the general formula (I):

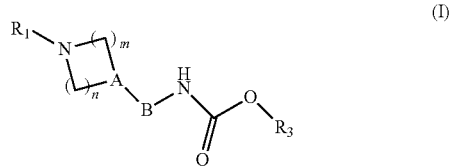

in which

A represents a nitrogen atom or a group $CR_2$ in which $R_2$ represents a hydrogen or fluorine atom or a hydroxyl, cyano, trifluoromethyl, $C_{1-6}$-alkyl or $C_{1-6}$-alkoxy group;

n represents an integer equal to 2 or 3 and m represents an integer equal to 2 when A represents a nitrogen atom;

n represents an integer equal to 1, 2 or 3 and m represents an integer equal to 1 or 2 when A represents a group $CR_2$;

B represents a covalent bond or a $C_{1-8}$-alkylene group;

$R_1$ represents a group chosen from phenyl, pyridyl, pyridazinyl, pyrimidinyl, pyrazinyl, triazinyl, oxazolyl, isoxazolyl, thiazolyl, isothiazolyl, imidazolyl, oxadiazolyl, thiadiazolyl, triazolyl, naphthyl, quinolyl, tetrahydroquinolyl, isoquinolyl, tetrahydroisoquinolyl, phthalazinyl, quinazolinyl, quinoxalinyl, naphthyridinyl, cinnolyl, imidazopyrimidinyl, thienopyrimidinyl, benzofuranyl, benzothienyl, benzimidazolyl, benzoxazolyl, benzisoxazolyl, benzothiazolyl, benzisothiazolyl, indazolyl, pyrrolopyridyl, furopyridyl, dihydrofuropyridyl, thienopyridyl, dihydrothienopyridyl, imidazopyridyl, pyrazolopyridyl, oxazolopyridyl, isoxazolopyridyl and thiazolopyridyl;

the group $R_1$ optionally being substituted with one or more groups R' and/or R";

R' represents a halogen atom or a cyano, nitro, hydroxyl, $C_{1-6}$-alkyl, $C_{1-6}$-alkoxy, $C_{1-6}$-thioalkyl, $C_{1-6}$-fluoroalkyl, $C_{1-6}$-fluoroalkoxy, $C_{1-6}$-fluorothioalkyl, $C_{3-7}$-cycloalkyl, $C_{3-7}$-cycloalkyl-$C_{1-6}$-alkylene, azetidinyl, piperidyl, pyrrolidinyl, morpholinyl, piperazinyl, azepinyl, $NH_2$, $NHR_6$, $NR_6R_7$, $NR_6COR_7$, $NR_6SO_2R_7$, $COR_6$, $CO_2R_6$, $SO_2R_6$, $SO_2NR_6R_7$ or —O—($C_{1-6}$-alkylene)—O— group;

R" represents a phenyl, imidazolyl, pyridyl, pyridazinyl, pyrazinyl or pyrimidinyl; the group(s) R" being optionally substituted with one or more groups R', which may be identical to or different from each other;

$R_3$ represents a group of general formula $CHR_4CONHR_5$ in which $R_4$ represents a hydrogen atom or a $C_{1-6}$-alkyl group and $R_5$ represents a hydrogen atom or a $C_{1-6}$-alkyl, $C_{3-7}$-cycloalkyl or $C_{3-7}$-cycloalkyl-$C_{1-6}$-alkylene group;

$R_6$ and $R_7$ represent, independently of each other, a $C_{1-6}$-alkyl group.

DETAILED DESCRIPTION

Among the compounds of general formula (I), a first subgroup of compounds consists of compounds for which:

A represents a nitrogen atom; and/or n represents an integer equal to 2 or 3 and m represents an integer equal to 2; and/or B represents a $C_{1-8}$-alkylene group, more particularly an ethyl or propyl; and/or $R_1$ represents a group chosen from phenyl, pyridyl, pyrimidinyl, thiadiazolyl and naphthyl;

the group $R_1$ being optionally substituted with one or more groups R' and/or R"; and/or R' represents a halogen atom, more particularly a chlorine, or a nitro or $C_{1-6}$-fluoroalkyl group, more particularly a trifluoromethyl; and/or R" represents a phenyl optionally substituted with one or more groups, which may be identical to or different from each other, chosen from a halogen atom, more particularly a chlorine, and a cyano, $C_{1-6}$-alkoxy, more particularly a methoxy, or $C_{1-6}$-fluoroalkoxy, more particularly a trifluoromethoxy, group; and/or $R_3$ represents a group of general formula $CHR_4CONHR_5$ in which $R_4$ represents a hydrogen atom and $R_5$ represents a hydrogen atom or a $C_{1-6}$-alkyl group, more particularly a methyl or an ethyl, a $C_{3-7}$-cycloalkyl group, more particularly a cyclopropyl, or a $C_{3-7}$-cycloalkyl-$C_{1-6}$-alkylene group, more particularly a cyclopropyl-methylene.

Among the compounds of general formula (I), a second subgroup of compounds consists of compounds for which:

A represents a group $CR_2$ in which $R_2$ represents a hydrogen or fluorine atom or a hydroxyl group; and/or m represents an integer equal to 1 or 2 and n represents an integer equal to 1 or 2; and/or B represents a covalent bond or a $C_{1-4}$-alkylene group, more particularly a methyl, ethyl or n-propyl; and/or $R_1$ represents a group chosen from phenyl, pyridyl, pyridazinyl, pyrimidinyl, pyrazinyl, thiazolyl, quinolyl, isoquinolyl, phthalazinyl, quinazolinyl, quinoxalinyl, naphthyridinyl, furopyridyl, thienopyrimidinyl, imidazopyrimidinyl, benzothiazolyl, benzimidazolyl and benzoxazolyl;

the group $R_1$ being optionally substituted with one or more groups R' and/or R"; and/or R' represents a halogen atom, more particularly a fluorine, a chlorine or a bromine, or a cyano group, $C_{1-6}$-alkyl, more particularly a methyl, ethyl, n-propyl or isobutyl, a $C_{1-6}$-alkoxy, more particularly a methoxy, $C_{1-6}$-fluoroalkyl, more particularly a trifluoromethyl, $C_{1-6}$-fluoroalkoxy, more particularly a trifluoromethoxy, $C_{3-7}$-cycloalkyl, more particularly a cyclopropyl or cyclopentyl, pyrrolidinyl, $NH_2$, $NR_6R_7$ or $COR_6$; and/or R" represents a phenyl, imidazolyl or pyridyl; the group(s) R" being optionally substituted with one or more groups R', which may be identical to or different from each other, more particularly with one or more chlorine or fluorine atoms; and/or $R_3$ represents a group of general formula $CHR_4CONHR_5$ in which $R_4$ represents a hydrogen atom or a $C_{1-6}$-alkyl group, more particularly a methyl, and $R_5$ represents a hydrogen atom or a $C_{1-6}$-alkyl group, more particularly a methyl or an ethyl, $C_{3-7}$-cycloalkyl, more particularly a cyclopropyl, $C_{3-7}$-cycloalkyl-$C_1$-$C_6$-alkylene, more particularly a cyclopropyl-methylene; and/or $R_6$ and $R_7$ represent, independently of each other, a $C_{1-6}$-alkyl group, more particularly a methyl.

Among the compounds of general formula (I), a third subgroup of compounds consists of compounds for which:

A represents a group $CR_2$ in which $R_2$ represents a hydrogen atom; and/or m is equal to 2 and n is equal to 2; and/or B represents an ethyl group; and/or $R_1$ represents a group chosen from phenyl, pyridyl, pyridazinyl, pyrimidinyl, pyrazinyl, thiazolyl, quinolyl, isoquinolyl, phthalazinyl, quinazolinyl, quinoxalinyl, naphthyridinyl, furopyridyl, thienopyrimidinyl, imidazopyrimidinyl, benzothiazolyl, benzimidazolyl and benzoxazolyl;

the group $R_1$ being optionally substituted with one or more groups R' and/or R"; and/or R' represents a halogen atom, more particularly a fluorine, a chlorine or a bromine, or a cyano group, $C_{1-6}$-alkyl, more particularly a methyl, ethyl, n-propyl or isobutyl, a $C_{1-6}$-alkoxy, more particularly a methoxy, $C_{1-6}$-fluoroalkyl, more particularly a trifluoromethyl, $C_{1-6}$-fluoroalkoxy, more particularly a trifluoromethoxy, $C_{3-7}$-cycloalkyl, more particularly a cyclopropyl or cyclopentyl, pyrrolidinyl, $NH_2$, $NR_6R_7$ or $COR_6$; and/or R" represents a phenyl, imidazolyl or pyridyl;

the group(s) R" being optionally substituted with one or more groups R', which may be identical to or different from each other, more particularly with one or more chlorine or fluorine atoms; and/or $R_3$ represents a group of general formula $CHR_4CONHR_5$ in which $R_4$ represents a hydrogen atom and $R_5$ represents a hydrogen atom or a $C_1$-$C_6$-alkyl group, more particularly a methyl or an ethyl; and/or $R_6$ and $R_7$ represent, independently of each other, a $C_{1-6}$-alkyl group, more particularly a methyl.

A subject of the invention is also, among the compounds of general formula (I), compounds corresponding to the general formula (I'):

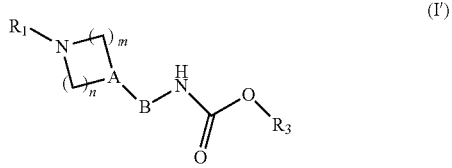

in which

A represents a nitrogen atom or a group $CR_2$ in which $R_2$ represents a hydrogen or fluorine atom or a hydroxyl, cyano, trifluoromethyl, $C_{1-5}$-alkyl or $C_{1-5}$-alkoxy group;

n represents an integer equal to 2 or 3 and m represents an integer equal to 2 when A represents a nitrogen atom;

n represents an integer equal to 1, 2 or 3 and m represents an integer equal to 1 or 2 when A represents a group $CR_2$;

B represents a covalent bond or a $C_{1-8}$-alkylene group;

$R_1$ represents a group chosen from phenyl, pyridyl, pyridazinyl, pyrimidinyl, pyrazinyl, triazinyl, thiazolyl, imidazolyl, oxadiazolyl, thiadiazolyl, triazolyl, naphthyl, quinolyl, tetrahydroquinolyl, isoquinolyl, tetrahydroisoquinolyl, phthalazinyl, quinazolinyl, quinoxalinyl, naphthyridinyl, cinnolyl, imidazopyrimidinyl, thienopyrimidinyl, benzofuranyl, benzothienyl, benzimidazolyl, benzoxazolyl, benzisoxazolyl, benzothiazolyl, benzisothiazolyl, indazolyl, pyrrolopyridyl, furopyridyl, dihydrofuropyridyl, thienopyridyl, dihydrothienopyridyl, imidazopyridyl, pyrazolopyridyl, oxazolopyridyl, isoxazolopyridyl and thiazolopyridyl;

optionally substituted with one or more substituents chosen from a halogen atom and a cyano, nitro, $C_{1-5}$-alkyl, $C_{1-3}$-alkoxy, $C_{1-5}$-thioalkyl, $C_{1-5}$-fluoroalkyl, $C_{1-3}$-fluoroalkoxy, $C_{1-3}$-fluorothioalkyl, $C_{3-5}$-cycloalkyl, $C_{3-5}$-cycloalkyl-$C_{1-3}$-alkylene, piperidyl, pyrrolidinyl, morpholinyl, $NH_2$, $NHR_6$, $NR_6R_7$, $NHCOR_6$, $COR_6$, $CO_2R_6$, $SO_2R_6$, —O—($C_{1-3}$-alkylene)—O—, phenyl, pyridyl or pyrimidinyl group;

the phenyl, pyridyl and pyrimidinyl groups possibly being substituted with one or more substituents chosen from a halogen atom and a cyano, nitro, hydroxyl, $C_{1-5}$-alkyl, $C_{1-3}$-alkoxy, $C_{1-5}$-thioalkyl, $C_{1-5}$-fluoroalkyl, $C_{1-3}$-fluoroalkoxy, $C_{1-3}$-fluorothioalkyl, $C_{3-5}$-cycloalkyl, $C_{3-5}$-cycloalkyl-$C_{1-3}$-alkylene, piperidyl, pyrrolidinyl, morpholinyl, $NH_2$, $NHR_6$, $NR_6R_7$, $NHCOR_6$, $COR_6$, $CO_2R_6$, $SO_2R_6$, or —O—($C_{1-3}$-alkylene)—O— group;

$R_3$ represents a group of general formula $CHR_4CONHR_5$ in which $R_4$ represents a hydrogen atom or a $C_{1-3}$-alkyl group and $R_5$ represents a hydrogen atom or a $C_{1-3}$-alkyl, $C_{3-5}$-cycloalkyl or $C_{3-5}$-cycloalkyl-$C_{1-3}$-alkylene group;

$R_6$ and $R_7$ represent, independently of each other, a $C_{1-3}$-alkyl group.

The compounds of general formula (I) may comprise one or more asymmetric carbons. They may exist in the form of enantiomers or diastereoisomers. These enantiomers and diastereoisomers, and also mixtures thereof, including racemic mixtures, form part of the invention.

The compounds of general formula (I) may exist in the form of bases or of acid-addition salts. Such addition salts form part of the invention.

These salts are advantageously prepared with pharmaceutically acceptable acids, but the salts of other acids that are useful, for example, for the purification or isolation of the compounds of formula (I) also form part of the invention.

The compounds of general formula (I) may be in the form of hydrates or solvates, i.e. in the form of associations or combinations with one or more water molecules or with a solvent. Such hydrates and solvates also form part of the invention.

In the context of the invention, the following definitions apply:

$C_{t-z}$ in which t and z may take values from 1 to 8, a carbon-based chain possibly containing from t to z carbon atoms, for example a $C_{1-3}$ carbon-based chain which may contain from 1 to 3 carbon atoms, alkyl, a saturated, linear or branched aliphatic group, for example a $C_{1-3}$-alkyl group represents a linear or branched carbon-based chain of 1 to 3 carbon atoms, more particularly a methyl, ethyl, propyl or 1-methylethyl, alkylene, a saturated, linear or branched divalent alkyl group, for example a $C_{1-3}$-alkylene group represents a linear or branched divalent carbon-based chain of 1 to 3 carbon atoms, more particularly a methylene, ethylene, 1-methylethylene or propylene, cycloalkyl, a cyclic alkyl group, for example a $C_{3-5}$-cycloalkyl group represents a cyclic carbon-based group of 3 to 5 carbon atoms, more particularly a cyclopropyl, cyclobutyl or cyclopentyl, alkoxy, an —O-alkyl group containing a saturated, linear or branched aliphatic chain, thioalkyl, an —S-alkyl group containing a saturated, linear or branched aliphatic chain, fluoroalkyl, an alkyl group in which one or more hydrogen atoms have been replaced with a fluorine atom,
fluoroalkoxy, an alkoxy group in which one or more hydrogen atoms have been replaced with a fluorine atom,
fluorothioalkyl, a thioalkyl group in which one or more hydrogen atoms have been replaced with a fluorine atom,
halogen atom, a fluorine, a chlorine, a bromine or an iodine.

The compounds of the invention may be prepared according to various methods, illustrated by the schemes that follow.

Thus, a first method (Scheme 1) consists in reacting an amine of general formula (II), in which A, B, $R_1$, n and m are as defined above, with a carbonate of general formula (IIIa) in which Z represents a hydrogen atom or a nitro group, $R_4$ is as defined above and R represents a methyl or ethyl group. The carbamate ester of general formula (Ia) thus obtained is then converted into a compound of general formula (I), via aminolysis using an amine of general formula $R_5NH_2$ in which $R_5$ is as defined above. The aminolysis reaction may be performed in a solvent such as methanol or a mixture of solvents such as methanol and tetrahydrofuran or methanol and dioxane.

One variant for obtaining the compounds of general formula (I) (Scheme 1) consists in reacting an amine of general formula (II), as defined above, with a carbonate of general formula (IIIb), in which Z represents a hydrogen atom or a nitro group and $R_4$ and $R_5$ are as defined above, in a solvent such as toluene or dichloroethane, at a temperature of between 0° C. and 80° C.

The carbonates of general formula (IIIa) and (IIIb) may be prepared according to any method described in the literature, for example by reacting an alcohol of general formula $HOCHR_4COOR$, in which R represents a methyl or ethyl group, or $HOCHR_4CONHR_5$ in which $R_4$ and $R_5$ are as defined above, with phenyl chloroformate or 4-nitrophenyl chloroformate, in the presence of a base such as triethylamine or diisopropylethylamine.

A second method for obtaining the compounds of general formula (I) (Scheme 2) consists in reacting a derivative of general formula (IIa) in which Y represents a hydroxyl, mesylate or tosylate group or a chlorine, bromine or iodine atom and A, B, $R_1$, n and m are as defined above, with an oxazolidinedione of general formula (IV) in which $R_4$ is as defined above, to give the oxazolidinedione derivative of general formula (V). In the case where Y represents a hydroxyl group, the reaction may be performed according to the Mitsunobu conditions (Synthesis, 1981, 1-28), for example via the action of diethyl or diisopropyl azodicarboxylate in the presence of triphenylphosphine. In the case where Y represents a chlorine, bromine or iodine atom or a mesylate or tosylate group, the reaction may be performed in the presence of a base such as 1,1,3,3-tetramethylguanidine, sodium hydride or sodium tert-butoxide in a solvent such as tetrahydrofuran, acetonitrile or dimethylformamide, at a temperature of between 0° C. and the reflux temperature of the solvent. The oxazolidinedione derivative of general formula (V) thus obtained is then converted into a compound of general formula (I), via aminolysis using an amine of general formula $R_5NH_2$ in which $R_5$ is as defined above.

Scheme 2

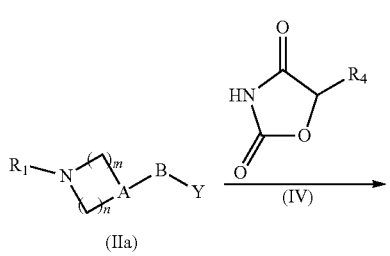

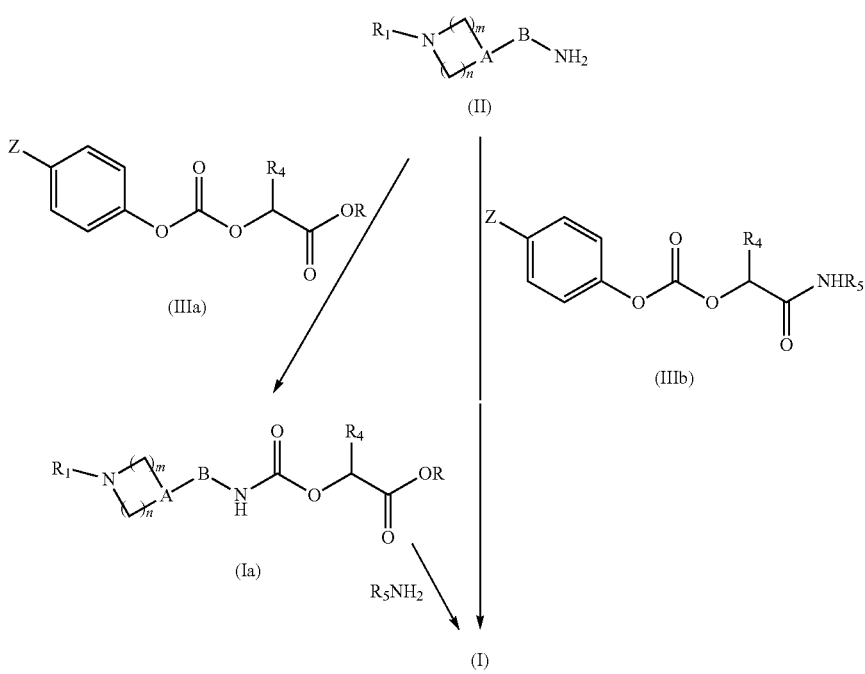

Scheme 1

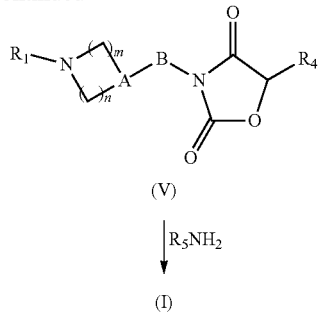

(V)

↓ R₅NH₂

(I)

The compounds of general formulae (I), (Ia), (II), (IIa) and (V), in which R₁ is substituted with a group R″, may also be prepared by reacting the corresponding compounds of general formulae (I), (Ia), (II), (IIa) and (V), for which R₁ is substituted with a chlorine, bromine or iodine atom or with a triflate group in the position into which the group R″ is to be introduced, with an aryl- or heteroarylboronic acid derivative according to the Suzuki reaction conditions (Chem. Rev. 1995, 95, 2457-2483) or with an aryl- or heteroaryl-trialkylstannane derivative according to the Stille reaction conditions (Angew. Chem. Int. Ed. 1986, 25, 504-524).

The compounds of general formulae (II), (IIa) and (IV), when their preparation method is not described, are commercially available or are described in the literature, or alternatively may be prepared according to methods that are described therein or known to those skilled in the art.

The amines of general formula R₅NH₂ are commercially available.

According to another of its aspects, a subject of the invention is also the compounds of formula (Ia) in which n, m, A, B, R₁ and R₄ are as defined above and R represents a methyl or ethyl group. The compounds of formula (Ia) are useful as synthetic intermediates for the preparation of the compounds of formula (I).

According to another of its aspects, a subject of the invention is also the compounds of formula (V) in which n, m, A, B, R₁ and R₄ are as defined above, the following compounds being excluded:
3-[1-(4-amino-6,7-dimethoxy-2-quinazolinyl)-4-piperidyl]-2,4-oxazolidinedione
3-[1-(4-amino-6,7-dimethoxy-2-quinazolinyl)-4-piperidyl]-5-methyl-2,4-oxazolidinedione
3-[1-(4-amino-6,7-dimethoxy-2-quinazolinyl)-4-piperidyl]-5-ethyl-2,4-oxazolidinedione
3-[1-(4-amino-6,7-dimethoxy-2-quinazolinyl)-4-piperidyl-]5-propyl-2,4-oxazolidinedione
3-[1-(4-amino-6,7-dimethoxy-2-quinazolinyl)-4-piperidyl]-5-(1-methylethyl)-2,4-oxazolidinedione.

The compounds of formula (V) are useful as synthetic intermediates for the preparation of the compounds of formula (I).

The examples that follow illustrate the preparation of a number of compounds of the invention. These examples are not limiting and are given merely to illustrate the invention. The microanalyses and the IR, NMR and/or LC/MS (Liquid Chromatography coupled to Mass Spectroscopy) spectra confirm the structures and purities of the compounds obtained.

m.p. (° C.) represents the melting point in degrees Celsius.

The numbers indicated in parentheses in the example titles correspond to those in the first column of the table hereinbelow.

The IUPAC (International Union of Pure and Applied Chemistry) nomenclature has been used for the naming of the compounds in the examples that follow.

EXAMPLE 1

Compound 38

2-(Methylamino)-2-oxoethyl 2-[4-(1-naphthyl)-1-piperazinyl]ethylcarbamate hydrochloride

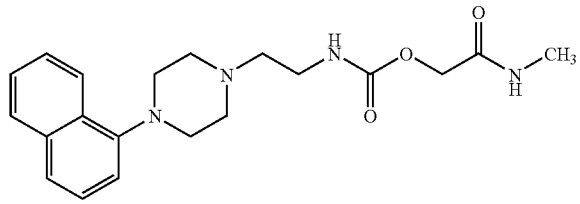

1.1. 2-{2-[4-(1-Naphthyl)-1-piperazinyl]ethyl}-1H-isoindole-1,3(2H)-dione

A suspension of 1.17 g (5.52 mmol) of 1-(1-naphthyl)piperazine (Tetrahedron Letters, 1998, 39(15), 2219-2222), 0.99 g (7.15 mol) of potassium carbonate and 1.68 g (6.62 mmol) of 2-(2-bromoethyl)-1H-isoindole-1,3(2H)-dione in 15 ml of N,N-dimethylformamide is heated at 90° C. for 2 hours.

The mixture is allowed to cool to room temperature and is concentrated under reduced pressure. The residue is taken up in ethyl acetate and water, the aqueous phase is separated out and extracted three times with ethyl acetate, and the combined organic phases are washed with saturated aqueous sodium chloride solution and dried over sodium sulfate. After evaporating off the solvent, the residue obtained is purified by chromatography on silica gel, eluting with a 40/60 mixture of ethyl acetate and cyclohexane.

1.14 g of pure product are thus obtained in the form of an oil.

1.2. 2-[4-(1-Naphthyl)-1-piperazinyl]ethanamine 0.17 ml (3.55 mmol) of hydrazine monohydrate is added slowly at room temperature to a solution of 1.14 g (2.96 mmol) of 2-{2-[4-(1-naphthyl)-1-piperazinyl]ethyl}-1H-isoindole-1,3(2H)-dione, prepared in step 1.1, in 15 ml of ethanol. The reaction mixture is then refluxed for 1 hour.

The mixture is allowed to cool to room temperature, the insoluble material is separated out by filtration and the filtrate is concentrated under reduced pressure. The residue is taken up in 20 ml of ether and stirred at room temperature for 20 minutes. The insoluble material is again separated out and the filtrate is concentrated under reduced pressure. The residue obtained is purified by chromatography on silica gel, eluting with a 90/10/1 mixture of dichloromethane, methanol and 28% aqueous ammonia.

0.45 g of amine is thus obtained in the form of a colourless oil.

1.3. Ethyl [(phenyloxycarbonyl)oxy]acetate 32 ml (256 mmol) of phenyl chloroformate are added slowly at room temperature to a solution of 25 g (240 mmol) of ethyl glycolate and 55 ml (315 mmol) of diisopropylethylamine in 500 ml of toluene. Stirring is continued at room temperature for 2 hours.

The salt formed is separated out and the filtrate is concentrated under reduced pressure.

53.7 g of oily product are obtained, and are used without further purification in the following step.

1.4. Ethyl [({2,4-(1-naphthyl)-1-piperazinyl]ethyl}amino)carbonyl]oxyacetate A solution of 0.45 g (1.76 mmol) of 2-[4-(1-naphthyl)-1-piperazinyl]ethanamine, prepared in step 1.2, and 0.48 g (2.16 mmol) of ethyl [(phenyloxycarbonyl)oxy]acetate, obtained in step 1.3, in 15 ml of toluene is heated at 50° C. for 6 hours.

The mixture is allowed to cool to room temperature, the insoluble material is separated out by filtration and the filtrate is concentrated under reduced pressure. The residue is taken up in dichloromethane and water, the aqueous phase is separated out and extracted three times with dichloromethane, and the combined organic phases are washed with saturated aqueous sodium chloride solution and dried over sodium sulfate. After evaporating off the solvent, the residue obtained is purified by chromatography on silica gel, eluting with a 97/3 and then 93/7 mixture of dichloromethane and methanol. 0.49 g of pure product is thus obtained in the form of an oil.

1.5. 2-(Methylamino)-2-oxoethyl 2-[4-(1-naphthyl)-1-piperazinyl]ethylcarbamate 1.9 ml (3.75 mmol) of a solution (2M) of methylamine in tetrahydrofuran are added to a solution of 0.48 g (1.25 mmol) of ethyl [({2,4-(1-naphthyl)-1-piperazinyl]ethyl}amino)carbonyl]oxyacetate, prepared in step 1.4, in 5 ml of methanol. Stirring is continued at room temperature for 1 hour.

After concentrating under reduced pressure, the residue obtained is purified by chromatography on silica gel, eluting with a 97/3 mixture of dichloromethane and methanol. An oily residue is obtained, which is taken up with a solution of hydrochloric acid (5N) in isopropanol. The mixture is concentrated to dryness and the salt obtained is then recrystallized from a 1/1 mixture of acetone and diisopropyl ether.

0.23 g of pure monohydrochloride product is thus obtained in the form of a white solid.

LC-MS: M+H=371 m.p. (° C.): 166° C. $^1$H NMR (DMSO) δ (ppm): 2.55 (d, 3H); 3.20-3.75 (unresolved peak, 12H); 4.40 (s, 2H); 7.10 (d, 1H); 7.35-7.70 (unresolved peak, 4H); 7.80-8.05 (unresolved peak, 2H); 8.15 (dd, 1H); 10.90 (broad s, 1H).

EXAMPLE 2

Compound 157

2-(Methylamino)-2-oxoethyl 3-[1-(1-isoquinolyl)-4-piperidyl]propylcarbamate hydrochloride

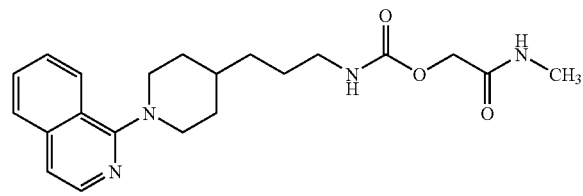

2.1. 2-[1-(1-Isoquinolyl)-4-piperidyl]ethanol 4.17 g (25.50 mmol) of 1-chloroisoquinoline, 3.62 g (28 mmol) of 2-(4-piperidyl)ethanol, 5.90 g (61.20 mmol) of sodium tert-butoxide and 0.476 g (0.765 mmol) of BINAP (2,2'-bis(diphenylphosphino)-1,1'-binaphthyl) suspended in 50 ml of toluene are introduced under an inert atmosphere. 0.233 g (0.255 mmol) of tris(dibenzylideneacetone)dipalladium is then added. The reaction mixture is then refluxed for 12 hours.

The salts are separated out by filtration through Celite and the filtrate is then concentrated under reduced pressure. The residue is taken up in ethyl acetate and water, the aqueous phase is separated out and extracted twice with ethyl acetate, and the combined organic phases are washed with saturated aqueous sodium chloride solution and dried over sodium sulfate. After evaporating off the solvent, the residue obtained is purified by chromatography on silica gel, eluting with a 97/3 mixture of dichloromethane and methanol.

3.34 g of product are obtained in the form of a grey paste.

2.2. 1-[4-(2-Chloroethyl)-1-piperidyl]isoquinoline 2.20 ml (30.10 mmol) of thionyl chloride are added dropwise to a solution of 3.09 g (12.10 mmol) of 2-[1-(1-isoquinolyl)-4-piperidyl]ethanol, prepared in step 2.1, in 30 ml of dichloromethane. The reaction mixture is then refluxed for 5 hours.

The mixture is concentrated to dryness under reduced pressure. The residue is taken up in 40 ml of dichloromethane and 30 ml of aqueous sodium hydroxide solution (1M). The aqueous phase is separated out and extracted twice with dichloromethane, the combined organic phases are washed with saturated aqueous sodium chloride solution and dried over sodium sulfate, and the filtrate is concentrated under reduced pressure. 2.70 g of product are obtained in the form of a brown paste, which is used without further purification in the following step.

2.3. 3-[1-(1-Isoquinolyl)-4-piperidyl]propanenitrile 0.63 g (9.57 mmol) of potassium cyanide is added portionwise to a suspension of 2.63 g (9.57 mmol) of 1-[4-(2-chloroethyl)-1-piperidyl]isoquinoline, prepared in step 2.2, and 0.048 g (0.29 mmol) of potassium iodide in 30 ml of dimethyl sulfoxide. The reaction mixture is maintained at about 120° C. for 16 hours. The mixture is allowed to cool to room temperature and 90 ml of water and ethyl acetate are then added. The aqueous phase is separated out and extracted three times with ethyl acetate, the combined organic phases are washed with saturated aqueous sodium chloride solution and dried over sodium sulfate, and the filtrate is concentrated under reduced pressure. The residue thus obtained is purified by chromatography on silica gel, eluting with a 30/70 mixture of ethyl acetate and cyclohexane.

0.77 g of product is obtained in the form of a yellow solid. m.p. (° C.): 141-143° C.

2.4. 3-[1-(1-Isoquinolyl)-4-piperidyl]propanamine

A solution of 0.77 g (2.90 mmol) of 3-[1-(1-isoquinolyl)-4-piperidyl]propanenitrile, prepared in step 2.3, in 16 ml of tetrahydrofuran is added dropwise to a suspension of 0.22 g (5.80 mmol) of lithium aluminium hydride in 8 ml of tetrahydrofuran. The reaction mixture is then refluxed for 5 hours.

The reaction medium is cooled to about 0° C. and 15 ml of aqueous sodium hydroxide solution (1M) are then added slowly. The mixture is stirred at room temperature for 30 minutes, followed by portionwise addition of wet sodium sulfate. The salts are separated out by filtration through paper and the phases are then allowed to separate by settling. The aqueous phase is extracted three times with ethyl acetate, the combined organic phases are dried over sodium sulfate and the filtrate is concentrated under reduced pressure. The residue thus obtained is purified by chromatography on silica gel, eluting with a 93/7/0.7 mixture of dichloromethane, methanol and 28% aqueous ammonia.

0.329 g of product is obtained in the form of a yellow oil that crystallizes at room temperature.

2.5. Ethyl [{3-[1-(1-isoquinolyl)-4-piperidyl]propyl}amino)carbonyl]oxyacetate The process is performed as in Example 1 (step 1.4). Starting with 0.350 g (1.30 mmol) of 3-[1-(1-isoquinolyl)-4-piperidyl]propanamine, obtained in step 2.4, and 0.32 g (1.43 mmol) of ethyl [(phenyloxycarbonyl)oxy]acetate, prepared in step 1.3 of Example 1, and after chromatography on silica gel, eluting with a 20/80 and then 30/70 mixture of ethyl acetate and cyclohexane, 0.383 g of product is obtained in the form of a yellow paste.

2.6. 2-(Methylamino)-2-oxoethyl 3-[1-(1-isoquinolyl)-4-piperidyl]propylcarbamate The process is performed as described in Example 1 (step 1.5). Starting with 0.380 g (0.95 mmol) of ethyl [{3-[1-(1-isoquinolyl)-4-piperidyl]propyl}amino)carbonyl]oxyacetate, obtained in step 2.5, and 4.8 ml (9.51 mmol) of a solution (2M) of methylamine in tetrahydrofuran, and after chromatography on silica gel, eluting with a 98/2 and then 95/5 mixture of dichloromethane and methanol, 0.277 g of product is obtained in the form of an oil. This oily residue is then taken up in a solution of hydrochloric acid (5N) in isopropanol and the salt formed is filtered off and then washed with ethyl acetate.

After drying under vacuum at about 40° C., 0.204 g of hydrochloride is obtained in the form of an amorphous white solid.

LC-MS: M+H=385 $^1$H NMR (DMSO+D$_2$O) δ (ppm): 1.30 (m, 2H); 1.40-1.80 (unresolved peak, 5H); 1.90 (broad d, 2H); 2.60 (s, 3H); 3.05 (m, 2H); 3.40 (t, 2H); 4.05 (broad d, 2H); 4.30 (s, 2H); 7.50 (d, 1H); 7.80 (m, 2H); 7.95 (t, 1H); 8.05 (d, 1H); 8.20 (d, 1H).

EXAMPLE 3

Compound 44

2-Amino-2-oxoethyl 2-{1-[3-(trifluoromethyl)phenyl]-4-piperidyl}ethylcarbamate

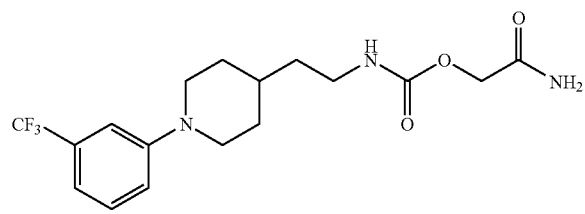

3.1. 2-{1-[3-(Trifluoromethyl)phenyl]-4-piperidyl}ethanol

The process is performed as described in Example 2 (step 2.1). Starting with 25.6 g (113.90 mmol) of 1-bromo-3-(trifluoromethyl)benzene, 17.66 g (136.60 mmol) of 2-(4-piperidyl)ethanol, 26.24 g (273 mmol) of sodium tert-butoxide, 2.12 g (3.41 mmol) of BINAP and 1.04 g (1.14 mmol) of tris-(dibenzylideneacetone)dipalladium, and after chromatography on silica gel, eluting with a 25/75 mixture of ethyl acetate and cyclohexane, 17.90 g of an orange-coloured oily residue are obtained. This residue is then taken up in 100 ml of methanol, a solution of 4.24 g of potassium hydroxide in 15 ml of methanol is then added and stirring is continued at room temperature for 1 hour. The mixture is concentrated under reduced pressure and the residue is then taken up in chloroform and aqueous hydrochloric acid solution (1N). The organic phase is separated out and dried over sodium sulfate, and the filtrate is concentrated under reduced pressure. 14 g of product are obtained in the form of a dark yellow oil, which is used without further purification in the following step.

3.2. 2-{1-[3-(Trifluoromethyl)phenyl]-4-piperidyl}ethyl methanesulfonate

A solution of 1 g (8.78 mmol) of mesyl chloride in 5 ml of dichloromethane is added dropwise under an inert atmosphere to a solution of 2 g (7.32 mmol) of 2-{1-[3-(trifluoromethyl)phenyl]-4-piperidyl}ethanol, obtained in step 3.1, and 1.53 ml (10.98 mmol) of triethylamine in 40 ml of dichloromethane, cooled to about 0° C. Stirring is continued at 0° C. for 1 hour and then at room temperature for 2 hours.

Water is added to the reaction medium, the aqueous phase is separated out and extracted three times with dichloromethane, the combined organic phases are washed with saturated aqueous sodium chloride solution and dried over sodium sulfate, and the filtrate is concentrated under reduced pressure.

2.5 g of product are thus obtained in the form of an oil, which is used without further purification in the following step.

3.3. 3-(2-{1-[3-(Trifluoromethyl)phenyl]-4-piperidyl}ethyl)-1,3-oxazolidine-2,4-dione A solution of 2.3 g (6.545 mmol) of 2-{1-[3-(trifluoromethyl)phenyl]-4-piperidyl}ethyl methanesulfonate, prepared in step 3.2, 0.694 g (6.87 mmol) of 1,3-oxazolidine-2,4-dione (J. Med. Chem., 1991, 34, 1538-1544) and 1.5 g (13.09 mmol) of 1,1,3,3-tetramethylguanidine in 30 ml of tetrahydrofuran is refluxed for 12 hours under an inert atmosphere.

The mixture is concentrated under reduced pressure. The residue is taken up in dichloromethane and water, the aqueous phase is separated out and extracted twice with dichloromethane, and the combined organic phases are washed with saturated aqueous sodium chloride solution and dried over sodium sulfate. After evaporating off the solvent, the residue obtained is purified by chromatography on silica gel, eluting with a 20/80 and then 40/60 mixture of ethyl acetate and cyclohexane.

1.61 g of pure product are obtained in the form of an oil.

3.4. 2-Amino-2-oxoethyl 2-{1-[3-(trifluoromethyl)phenyl]-4-piperidyl}ethylcarbamate 9.3 ml (64.82 mmol) of a solution of aqueous ammonia (7N) in methanol are added to a solution of 0.77 g (2.16 mmol) of 3-(2-{1-[3-(trifluoromethyl)phenyl]-4-piperidyl}ethyl)-1,3-oxazolidine-2,4-dione, obtained in step 3.3, in 10 ml of a 1/1 mixture of methanol and tetrahydrofuran. Stirring is continued at room temperature for 24 hours.

After concentrating under reduced pressure, the residue obtained is purified by chromatography on silica gel, eluting with a 97/3 and then 95/5 mixture of dichloromethane and methanol, followed by recrystallization from a mixture of ethyl acetate and diisopropyl ether.

0.370 g of pure product is obtained in the form of a white solid.

LC-MS: M+H=374 m.p. (° C.): 140-142° C. $^1$H NMR (CDCl$_3$) δ (ppm): 1.30-1.55 (unresolved peak, 5H); 1.90 (broad d, 2H); 2.80 (t, 2H); 3.35 (q, 2H); 3.80 (broad d, 2H); 4.60 (s, 2H); 4.90 (broad s, 1H); 5.55 (broad s, 1H); 6.05 (broad s, 1H); 7.10 (m, 3H); 7.35 (t, 1H).

EXAMPLE 4

Compound 47

2-(Methylamino)-2-oxoethyl 2-[1-(6-methyl-2-pyridyl)-4-piperidyl]ethylcarbamate hydrochloride

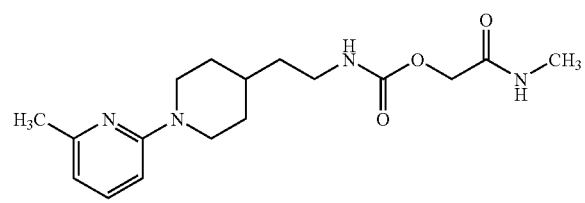

4.1. 2-[1-(6-Methyl-2-pyridyl)-4-piperidyl]ethanol 1 g (7.74 mmol) of 2-(4-piperidyl)ethanol and 0.987 g (7.74 mmol) of 2-chloro-6-methylpyridine are introduced into an autoclave. The mixture is then heated at 130° C. for 17 hours.

The reaction mixture is allowed to cool to room temperature and is then taken up in chloroform and saturated aqueous sodium hydrogen carbonate solution. The aqueous phase is separated out and extracted twice with chloroform, the combined organic phases are washed with saturated aqueous sodium chloride solution and dried over sodium sulfate, and the filtrate is concentrated under reduced pressure.

1.21 g of product are thus obtained in the form of an orange-coloured liquid, which is used without further purification in the following step.

4.2. 2-[1-(6-Methyl-2-pyridyl)-4-piperidyl]ethyl methanesulfonate

The process is performed as in Example 3 (step 3.2). Starting with 0.661 g (3 mmol) of 2-[1-(6-methyl-2-pyridyl)-4-piperidyl]ethanol, obtained in step 4.1, 0.378 g (3.30 mmol) of mesyl chloride and 0.63 ml (4.50 mmol) of triethylamine, 0.779 g of product is obtained in the form of an orange-coloured oil, which is used without further purification in the following step.

4.3. 3-{2-[1-(6-Methyl-2-pyridyl)-4-piperidyl]ethyl}-1,3-oxazolidine-2,4-dione The process is performed according to the method described in Example 3 (step 3.3). Starting with 0.776 g (2.60 mmol) of 2-[1-(6-methyl-2-pyridyl)-4-piperidyl]ethyl methanesulfonate, obtained in step 4.2, 0.315 g (3.12 mmol) of 1,3-oxazolidine-2,4-dione and 0.65 ml (5.20 mmol) of 1,1,3,3-tetramethylguanidine, and after chromatography on silica gel, eluting with a 30/70 mixture of ethyl acetate and cyclohexane, 0.76 g of pure product is obtained in the form of a yellow oil.

4.4. 2-(Methylamino)-2-oxoethyl 2-[1-(6-methyl-2-pyridyl)-4-piperidyl]ethylcarbamate The process is performed according to the procedure described in Example 1 (step 1.5). Starting with 0.841 g (2.77 mmol) of 3-{2-[1-(6-methyl-2-pyridyl)-4-piperidyl]ethyl}-1,3-oxazolidine-2,4-dione, obtained in step 4.3, and 6.9 ml (13.86 mmol) of a solution (2M) of methylamine in tetrahydrofuran, 0.598 g of pure product is obtained in the form of an oil, after chromatography on silica gel, eluting with a 95/5 mixture of dichloromethane and methanol. This oily residue is then taken up with a solution of hydrochloric acid (5N) in isopropanol and the salt formed is filtered off and then washed successively with acetone and then with ether.

After drying under vacuum at about 80° C., 0.492 g of hydrochloride is obtained in the form of a white powder.

LC-MS: M+H=335 m.p. (° C.): 95-100° C. $^1$H NMR (DMSO+D$_2$O) δ (ppm): 0.95-1.45 (unresolved peak, 4H); 1.60 (m, 1H); 1.80 (broad d, 2H); 2.40 (s, 3H); 2.60 (s, 3H); 2.90-3.20 (unresolved peak, 4H); 4.10 (broad d, 2H); 4.30 (s, 2H); 6.70 (d, 1H); 7.10 (d, 1H); 7.75 (dd, 1H).

EXAMPLE 5

Compound 154

2-(Methylamino)-2-oxoethyl [1-(1-isoquinolyl)-4-piperidyl]methylcarbamate hydrochloride

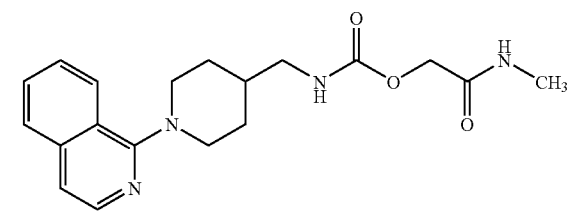

5.1. [1-(1-Isoquinolyl)-4-piperidyl]methanol

The process is performed as described in Example 2 (step 2.1). Starting with 2.50 g (15.28 mmol) of 1-chloroisoquinoline, 1.94 g (136.6 mmol) of 4-piperidylmethanol, 3.53 g (36.67 mmol) of sodium tert-butoxide, 0.285 g (0.46 mmol) of BINAP and 0.140 g (0.15 mmol) of tris(dibenzylideneacetone)dipalladium, and after chromatography on silica gel, eluting with a 98/2/0.2 and then 95/5/0.5 mixture of dichloromethane, methanol and 28% aqueous ammonia, 2.40 g of pure product are obtained in the form of a viscous orange oil.

5.2. 3-{[1-(1-Isoquinolyl)-4-piperidyl]methyl}-1,3-oxazolidine-2,4-dione

A solution of 2.01 g (9.95 mmol) of diisopropyl azodicarboxylate (DIAD) in 5 ml of tetrahydrofuran is added dropwise, under an inert atmosphere, to a solution of 2.4 g (9.95 mmol) of [1-(1-isoquinolyl)-4-piperidyl]methanol, prepared in step 5.1, 2.87 g (10.94 mmol) of triphenylphosphine and 1.21 g (11.93 mmol) of 1,3-oxazolidine-2,4-dione in 40 ml of tetrahydrofuran, cooled to about −10° C., the temperature of the reaction medium being maintained throughout between −10° C. and 0° C. Stirring is then continued at 0° C. for 1 hour and then at 25° C. for 18 hours.

The mixture is concentrated under reduced pressure and the residue is taken up in dichloromethane and 10 ml of aqueous 5% sodium hydroxide solution. The aqueous phase is separated out and then extracted twice with dichloromethane. The organic phases are combined and washed successively with aqueous hydrochloric acid solution (1N) and then with saturated aqueous sodium hydrogen carbonate solution and with saturated aqueous sodium chloride solution. The organic phase is dried over sodium sulfate and the filtrate is concentrated under reduced pressure. The residue thus obtained is purified by chromatography on silica gel, eluting with a 99/1/0.1 and then 98/2/0.2 mixture of dichloromethane, methanol and 28% aqueous ammonia.

3.57 g of oxazolidinedione are thus obtained in the form of an orange paste.

5.3. 2-(Methylamino)-2-oxoethyl [1-(1-isoquinolyl)-4-piperidyl]methylcarbamate The process is performed according to the procedure described in Example 1 (step 1.5). Starting with 3.57 g (10.97 mmol) of 3-{[1-(1-isoquinolyl)-4-piperidyl]methyl}-1,3-oxazolidine-2,4-dione, obtained in step 5.2, and 27 ml (54.86 mmol) of a solution (2M) of methylamine in tetrahydrofuran, and after chromatography on silica gel, eluting with a 95/5/0.5 mixture of dichloromethane, methanol and 28% aqueous ammonia, 0.90 g of pure product is obtained in the form of a yellow paste. This residue is then taken up in a solution of hydrochloric acid (5N) in isopropanol, and the salt formed is filtered off and then washed with acetone.

After drying under vacuum at about 80° C., 0.728 g of hydrochloride is obtained in the form of a pale yellow solid.

LC-MS: M+H=357 m.p. (° C.): 208-212° C. (decomposition) $^1$H NMR (D$_2$O) δ (ppm): 1.55 (m, 2H); 1.95 (m, 3H); 2.70 (s, 3H); 3.20 (broad d, 2H); 3.45 (t, 2H); 4.10 (broad d, 2H); 4.50 (s, 2H); 7.35 (d, 1H); 7.55 (d, 1H); 7.70 (m, 1H); 7.90 (d, 2H); 8.20 (d, 1H).

EXAMPLE 6

Compound 158

2-Amino-2-oxoethyl 2-[1-(6-fluoro-1-isoquinolyl)-4-piperidyl]ethylcarbamate

6.1. 2-[1-(6-Fluoro-1-isoquinolyl)-4-piperidyl]ethanol

The process is performed as described in Example 4 (step 4.1). Starting with 1.52 g (8.39 mmol) of 1-chloro-6-fluoroisoquinoline and 1.20 g (9.23 mmol) of 2-(4-piperidyl)ethanol, and after chromatography on silica gel, eluting with a 95/5/0.5 mixture of dichloromethane, methanol and 28% aqueous ammonia, 0.90 g of pure product is obtained in the form of a yellow paste.

6.2. 2-[1-(6-Fluoro-1-isoquinolyl)-4-piperidyl]ethyl methanesulfonate

The process is performed as described in Example 3 (step 3.2). Starting with 1.47 g (5.36 mmol) of 2-[1-(6-fluoro-1-isoquinolyl)-4-piperidyl]ethanol, obtained in step 6.1, 0.675 g (5.89 mmol) of mesyl chloride and 1.13 ml (8.04 mmol) of triethylamine, 1.80 g of product are obtained in the form of an oil, which is used without further purification in the following step.

6.3. 3-{2-[1-(6-Fluoro-1-isoquinolyl)-4-piperidyl]ethyl}-1,3-oxazolidine-2,4-dione The process is performed according to the method described in Example 3 (step 3.3). Starting with 1.8 g (5.10 mmol) of 2-[1-(6-fluoro-1-isoquinolyl)-4-piperidyl]ethyl methanesulfonate, obtained in step 6.2, 0.62 g (6.13 mmol) of 1,3-oxazolidine-2,4-dione and 1.30 ml (10.21 mmol) of 1,1,3,3-tetramethylguanidine, and after chromatography on silica gel, eluting with a 40/60 mixture of ethyl acetate and cyclohexane, 1.34 g of pure product are obtained in the form of an amorphous white solid.

6.4. 2-Amino-2-oxoethyl 2-[1-(6-fluoro-1-isoquinolyl)-4-piperidyl]ethylcarbamate The process is performed according to the procedure described in Example 3 (step 3.4). Starting with 0.597 g (1.67 mmol) of 3-{2-[1-(6-fluoro-1-isoquinolyl)-4-piperidyl]ethyl}-1,3-oxazolidine-2,4-dione, obtained in Step 6.3, and 14.30 ml (100.20 mmol) of a solution (7M) of aqueous ammonia in methanol, and after chromatography on silica gel, eluting with a 95/5 mixture of dichloromethane and methanol, followed by recrystallization from diisopropyl ether, 0.168 g of pure product is obtained in the form of a white solid.

LC-MS: M+H=375 m.p. (° C.): 135-139° C. $^1$H NMR (DMSO) δ (ppm): 1.20-1.70 (unresolved peak, 5H); 1.80 (broad d, 2H); 2.85 (t, 2H); 3.10 (broad d, 2H); 3.70 (broad d, 2H); 4.30 (s, 2H); 6.95-7.20 (unresolved peak, 3H); 7.30 (d, 1H); 7.45 (td, 1H); 7.60 (dd, 1H); 8.10 (m, 2H).

EXAMPLE 7

Compound 172

2-(Methylamino)-2-oxoethyl 2-[1-(4-isoquinolyl)-4-piperidyl]ethylcarbamate hydrochloride

7.1. 2-[1-(4-Isoquinolyl)-4-piperidyl]ethanol

The process is performed according to the protocol described in Example 2 (step 2.1). Starting with 1 g (4.81 mmol) of 4-bromoisoquinoline, 0.683 g (5.29 mmol) of 2-(4-piperidyl)ethanol, 1.11 g (11.50 mmol) of sodium tert-butoxide, 0.090 g (0.144 mmol) of BINAP and 0.044 g (0.048 mmol) of tris(dibenzylideneacetone)dipalladium, and after chromatography on silica gel, eluting with a 97/3 and then 95/5 mixture of dichloromethane and methanol, 0.810 g of product is obtained in the form of a viscous green liquid.

7.2. 3-{2-[1-(4-Isoquinolyl)-4-piperidyl]ethyl}-1,3-oxazolidine-2,4-dione

The procedure described in Example 5 (step 5.2) is used. Starting with 0.801 g (3.12 mmol) of 2-[1-(4-isoquinolyl)-4-piperidyl]ethanol, prepared in step 7.1, 0.902 g (3.44 mmol) of triphenylphosphine, 0.379 g (3.75 mmol) of 1,3-oxazolidine-2,4-dione and 0.632 g (3.12 mmol) of diisopropyl azodicarboxylate (DIAD), and after chromatography on silica gel, eluting with a 98/2 mixture of dichloromethane and methanol, 1 g of product is obtained in the form of a green paste.

7.3. 2-(Methylamino)-2-oxoethyl 2-[1-(4-isoquinolyl)-4-piperidyl]ethylcarbamate The procedure described in Example 1 (step 1.5) is used. Starting with 1 g (2.95 mmol) of 3-{2-[1-(4-isoquinolyl)-4-piperidyl]ethyl}-1,3-oxazolidine-2,4-dione, obtained in step 7.2, and 7.40 ml (14.73 mmol) of a solution (2M) of methylamine in tetrahydrofuran, and after chromatography on silica gel, eluting with a 95/5 mixture of dichloromethane and methanol, 0.410 g of pure product is obtained in the form of an amorphous white solid. This oily residue is then taken up in a solution of hydrochloric acid (5N) in isopropanol and the salt formed is filtered off and then washed successively with acetone and then with diisopropyl ether.

After drying under vacuum at about 90° C., 0.359 g of hydrochloride is obtained in the form of a yellow solid.

LC-MS: M+H=371 m.p. (° C.): 205-210° C. $^1$H NMR (DMSO) δ (ppm): 1.30-1.70 (unresolved peak, 5H); 1.90 (broad d, 2H); 2.60 (d, 3H); 2.90 (t, 2H); 3.15 (m, 2H); 3.50 (broad d, 2H); 4.35 (s, 2H); 7.25 (broad t, 1H); 7.80 (broad s, 1H); 8.0 (dd, 1H); 8.05-8.30 (unresolved peak, 3H); 8.45 (d, 1H); 9.45 (s, 1H).

EXAMPLE 8

Compound 126

2-(Methylamino)-2-oxoethyl 2-[1-(2-quinolyl)-4-piperidyl]ethylcarbamate

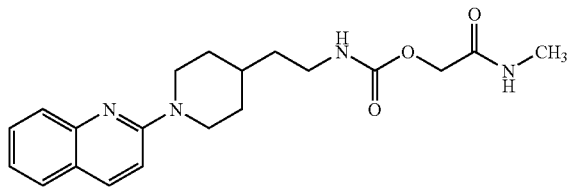

8.1. 2-[1-(2-Quinolyl)-4-piperidyl]ethanol

The process is performed as in Example 4 (step 4.1). Starting with 2 g (12.20 mmol) of 2-chloroquinoline and 1.58 g (12.20 mmol) of 2-(4-piperidyl)ethanol, and after chromatography on silica gel, eluting with a 98/2/0.2 and then 95/5/0.5 mixture of dichloromethane, methanol and 28% aqueous ammonia, 2.36 g of pure product are obtained in the form of a pale yellow oil that crystallizes at room temperature.

8.2. 3-{2-[1-(2-Quinolyl)-4-piperidyl]ethyl-1,3-oxazolidine-2,4-dione

The process is performed according to the procedure described in Example 5 (step 5.2). Starting with 2.22 g (8.65 mmol) of 2-[1-(2-quinolyl)-4-piperidyl]-ethanol, prepared in step 8.1, 2.50 g (9.52 mmol) of triphenylphosphine, 1.05 g (10.38 mmol) of 1,3-oxazolidine-2,4-dione and 1.75 g (8.65 mmol) of diisopropyl azodicarboxylate (DIAD), and after chromatography on silica gel, eluting with a 30/70 and then 40/60 mixture of ethyl acetate and cyclohexane, 2.63 g of product are obtained in the form of an amorphous white solid.

8.3. 2-(Methylamino)-2-oxoethyl 2-[1-(2-quinolyl)-4-piperidyl]ethylcarbamate The process is performed according to the procedure described in Example 1 (step 1.5). Starting with 1.5 g (4.42 mmol) of 3{2-[1-(2-quinolyl)-4-piperidyl]ethyl-1,3-oxazolidine-2,4-dione, obtained in step 8.2, and 11 ml (22.10 mmol) of a solution (2M) of methylamine in tetrahydrofuran, and after chromatography on silica gel, eluting with a 98/2/0.2 and then 95/5/0.5 mixture of dichloromethane, methanol and 28% aqueous ammonia, followed by crystallization from ethyl acetate, 0.405 g of pure product is obtained in the form of a white solid.

LC-MS: M+H=371 m.p. (° C.): 125-128° C. $^1$H NMR (CDCl$_3$) δ (ppm): 1.20-1.60 (unresolved peak, 5H); 1.85 (broad d, 2H); 2.85 (d, 3H); 3.0 (broad t, 2H); 3.30 (broad q, 2H); 4.55 (broad d, 2H); 4.60 (s, 2H); 4.85 (broad s, 1H); 6.10 (broad s, 1H); 7.0 (d, 1H); 7.20 (t, 1H); 7.55 (m, 2H); 7.70 (d, 1H); 7.90 (d, 1H).

EXAMPLE 9

Compound 127

2-Amino-2-oxoethyl 2-[1-(2-quinolyl)-4-piperidyl]ethylcarbamate

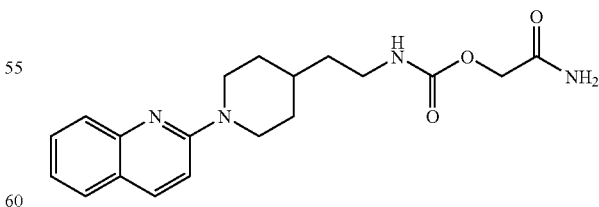

The process is performed according to the procedure described in Example 3 (step 3.4). Starting with 1.14 g (3.36 mmol) of 3{2-[1-(2-quinolyl)-4-piperidyl]ethyl}-1,3-oxazolidine-2,4-dione, described in Example 8 (step 8.2), and 9.60 ml (67.20 mmol) of a solution (7M) of aqueous ammonia in methanol, and after chromatography on silica gel, eluting with a 95/5 mixture of dichloromethane and methanol, followed by recrystallization from ethyl acetate, 0.360 g of pure product is obtained in the form of a white solid.

LC-MS: M+H=357 m.p. (° C.): 135-137° C. $^1$H NMR (CDCl$_3$) δ (ppm): 1.15-1.70 (unresolved peak, 5H); 1.85 (broad d, 2H); 2.95 (t, 2H); 3.35 (q, 2H); 4.55 (broad d, 2H); 4.60 (s, 2H); 4.85 (broad s, 1H); 5.55 (broad s, 1H); 6.05 (broad s, 1H); 7.0 (d, 1H); 7.20 (t, 1H); 7.55 (t, 1H); 7.60 (d, 1H); 7.70 (d, 1H); 7.90 (d, 1H).

EXAMPLE 10

Compound 137

2-Amino-2-oxoethyl 2-[1-(6-chloro-2-quinolyl)-4-piperidyl]ethylcarbamate

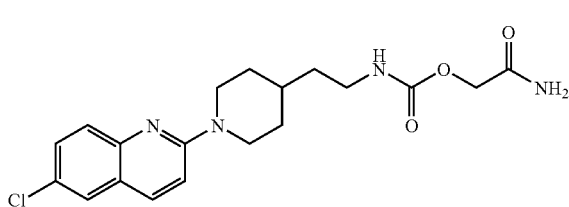

10.1. 2-[1-(6-Chloro-2-quinolyl)-4-piperidyl]ethanol

The process is performed as described in Example 4 (step 4.1). Starting with 2 g (10.10 mmol) of 2,6-dichloroquinoline and 1.44 g (11.10 mmol) of 2-(4-piperidyl)ethanol, and after chromatography on silica gel, eluting with a 98/2 mixture of dichloromethane and methanol, 2.54 g of pure product are obtained in the form of a white solid.

10.2. 2-[1-(6-Chloro-2-quinolyl)-4-piperidyl]ethyl methanesulfonate

The process is performed as described in Example 3 (step 3.2). Starting with 2.49 g (8.56 mmol) of 2-[1-(6-chloro-2-quinolyl)-4-piperidyl]ethanol, obtained in step 10.1, 1.08 g (9.42 mmol) of mesyl chloride and 1.81 ml (12.84 mmol) of triethylamine, 3.10 g of product are obtained in the form of an oil, which is used without further purification in the following step.

10.3. 3-{2-[1-(6-Chloro-2-quinolyl)-4-piperidyl]ethyl}-1,3-oxazolidine-2,4-dione The process is performed according to the method described in Example 3 (step 3.3). Starting with 3 g (8.13 mmol) of 2-[1-(6-chloro-2-quinolyl)-4-piperidyl]ethyl methanesulfonate, obtained in step 10.2, 1.09 g (10.8 mmol) of 1,3-oxazolidine-2,4-dione and 2.30 ml (18 mmol) of 1,1,3,3-tetramethylguanidine, and after chromatography on silica gel, eluting with a 98/2 mixture of dichloromethane and methanol, 2.57 g of product are obtained.

10.4. 2-Amino-2-oxoethyl 2-[1-(6-chloro-2-quinolyl)-4-piperidyl]ethylcarbamate

The process is performed according to the procedure described in Example 3 (step 3.4). Starting with 1.28 g (3.42 mmol) of 3-{2-[1-(6-chloro-2-quinolyl)-4-piperidyl]ethyl}-1,3-oxazolidine-2,4-dione, obtained in step 10.3, and 22.10 ml (154.08 mmol) of a solution (7M) of aqueous ammonia in methanol, and after crystallization from ethanol, 0.64 g of pure product is obtained in the form of a white solid.

LC-MS: M+H=391 m.p. (° C.): 189-191° C. $^1$H NMR (DMSO) δ (ppm): 1.10 (m, 2H); 1.40 (m, 2H); 1.60 (m, 1H); 1.80 (broad d, 2H); 2.90 (broad t, 2H); 3.05 (m, 2H); 4.30 (s, 2H); 4.50 (broad d, 2H); 7.15 (m, 3H); 7.25 (d, 1H); 7.50 (m, 2H); 7.75 (d, 1H); 7.95 (d, 1H).

EXAMPLE 11

Compound 166

2-(Methylamino)-2-oxoethyl 2-[1-(3-isoquinolyl)-4-piperidyl]ethylcarbamate

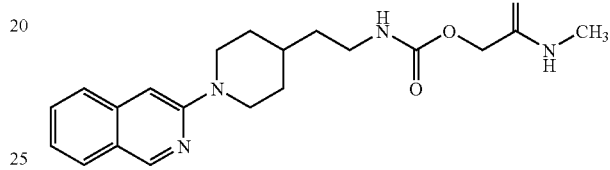

11.1. 2-[1-(3-Isoquinolyl)-4-piperidyl]ethanol

The process is performed as described in Example 4 (step 4.1). Starting with 1 g (6.11 mmol) of 3-chloroisoquinoline and 0.869 g (6.72 mmol) of 2-(4-piperidyl)ethanol, and after chromatography on silica gel, eluting with a 98/2 mixture of dichloromethane and methanol, 0.34 g of pure product is obtained in the form of an oil.

11.2. 2-[1-(3-Isoquinolyl)-4-piperidyl]ethyl methanesulfonate

The process is performed as described in Example 3 (step 3.2). Starting with 0.34 g (1.33 mmol) of 2-[1-(3-isoquinolyl)-4-piperidyl]ethanol, obtained in step 11.1, 0.18 g (1.59 mmol) of mesyl chloride and 0.30 ml (1.99 mmol) of triethylamine, 0.44 g of product is obtained in the form of an oil, which is used without further purification in the following step.

11.3. 3-{2-[1-(3-Isoquinolyl)-4-piperidyl]ethyl}-1,3-oxazolidine-2,4-dione

The process is performed according to the method described in Example 3 (step 3.3). Starting with 0.44 g (1.32 mmol) of 2-[1-(3-isoquinolyl)-4-piperidyl]-ethyl methanesulfonate, obtained in step 11.2, 0.16 g (1.58 mmol) of 1,3-oxazolidine-2,4-dione and 0.30 g (2.63 mmol) of 1,1,3,3-tetramethylguanidine, and after chromatography on silica gel, eluting with a 98/2 mixture of dichloromethane and methanol, 0.25 g of product is obtained.

11.4. 2-(Methylamino)-2-oxoethyl 2-[1-(3-isoquinolyl)-4-piperidyl]ethylcarbamate The process is performed according to the procedure described in Example 1 (step 1.5). Starting with 0.24 g (0.71 mmol) of 3-{2-[1-(3-isoquinolyl)-4-piperidyl]ethyl}-1,3-oxazolidine-2,4-dione, obtained in step 11.3, and 1.8 ml (3.53 mmol) of a solution (2M) of methylamine in tetrahydrofuran, and after chromatography on silica gel, eluting with a 98/2 and then 96/4 mixture of dichloromethane and methanol, followed by crystallization from diisopropyl ether, 0.16 g of pure product is obtained in the form of a white solid.

LC-MS: M+H=371 m.p. (° C.): 156-158° C. $^1$H NMR (CDCl$_3$) δ (ppm): 1.20-1.70 (unresolved peak, 5H); 1.85 (d, 2H); 2.90 (m, 5H); 3.30 (q, 2H); 4.40 (d, 2H); 4.60 (s, 2H); 4.85 (broad s, 1H); 6.10 (broad s, 1H); 6.80 (s, 1H); 7.30 (m, 1H); 7.60 (m, 2H); 7.80 (d, 1H); 8.95 (s, 1H).

EXAMPLE 12

Compound 128

2-(Methylamino)-2-oxoethyl 2-[4-fluoro-1-(2-quinolyl)-4-piperidyl]ethylcarbamate

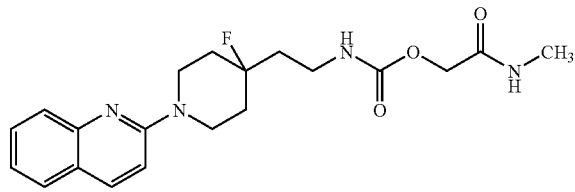

12.1. tert-Butyl 4-hydroxy-4-(2-hydroxyethyl)-1-piperidinecarboxylate

A solution of 31.20 g (108.50 mmol) of tert-butyl 4-(2-ethoxy-2-oxoethyl)-4-hydroxy-1-piperidinecarboxylate (WO 02/16352) in 150 ml of tetrahydrofuran is added dropwise to a suspension of 4.12 g (108.50 mmol) of lithium aluminium hydride in 150 ml of tetrahydrofuran. The mixture is stirred at room temperature for 2 hours and is then worked up as described in Example 2 (step 2.4).

26 g of product are obtained in the form of a yellow oil, which is used without further purification in the following step.

12.2. tert-Butyl 4-(2-{[tert-butyldiphenylsilyl]oxy}ethyl)-4-hydroxy-1-piperidine-carboxylate A solution of 21.50 ml (82.50 mmol) of tert-butyldiphenylsilyl chloride in 15 ml of dichloromethane is added dropwise, under an inert atmosphere, to a solution of 18.4 g (75 mmol) of tert-butyl 4-hydroxy-4-(2-hydroxyethyl)-1-piperidinecarboxylate, obtained in step 12.1, and 11.60 ml (82.50 mmol) of triethylamine in 100 ml of dichloromethane, cooled to about 0° C. The mixture is allowed to warm to room temperature and stifling is then continued for 12 hours. Saturated aqueous ammonium chloride solution is added to the reaction medium. The aqueous phase is separated out and extracted twice with dichloromethane, the combined organic phases are washed with saturated aqueous sodium chloride solution and dried over sodium sulfate, and the filtrate is concentrated under reduced pressure. The residue thus obtained is purified by chromatography on silica gel, eluting with a 10/90 and then 20/80 mixture of ethyl acetate and cyclohexane.

33.48 g of product are thus obtained in the form of a yellow oil.

12.3. tert-Butyl 4-(2-{[tert-butyl(diphenyl)silyl]oxy}ethyl)-4-fluoro-1-piperidinecarboxylate A solution of 1.70 ml (13.40 mmol) of 1,1'-[(trifluoro-λ$^4$-sulfanyl)imino]diethane (DAST) in 10 ml of dichloromethane is added dropwise, under an inert atmosphere, to a solution of 5 g (10.34 mmol) of tert-butyl 4-(2-{[tert-butyl(diphenyl)silyl]oxy}ethyl)-4-hydroxy-1-piperidinecarboxylate, obtained in step 12.2, in 100 ml of dichloromethane, cooled to about 0° C. The mixture is allowed to warm to room temperature and stirring is then continued for 12 hours. Saturated aqueous sodium hydrogen carbonate solution is added to the reaction medium. The aqueous phase is separated out and extracted three times with dichloromethane, and the combined organic phases are washed with saturated aqueous sodium chloride solution and dried over sodium sulfate. The filtrate is concentrated under reduced pressure and the residue thus obtained is then purified by chromatography on silica gel, eluting with a 10/90 mixture of ethyl acetate and cyclohexane. 4.65 g of product are thus obtained in the form of an orange-coloured oil. 0.60 ml of a solution of osmium tetroxide (2.5%) in tert-butanol is added at room temperature to a solution of 4.50 g of this oily residue and 1.25 g (10.7 mmol) of N-methylmorpholine oxide (NMO) in a mixture of 8 ml of acetone and 6 ml of water. Stirring is continued for 21 hours. The residue is taken up in ethyl acetate and water, the aqueous phase is separated out and extracted twice with ethyl acetate, and the combined organic phases are washed with saturated aqueous sodium chloride solution and dried over sodium sulfate. After evaporating off the solvent, the residue obtained is purified by chromatography on silica gel, eluting with a 6/94 mixture of ethyl acetate and cyclohexane.

3.40 g of product are thus obtained in the form of a pale yellow oil.

12.4. 4-(2-{[tert-butyl(diphenyl)silyl]oxy}ethyl)-4-fluoropiperidine 2.80 ml (37.06 mmol) of trifluoroacetic acid are added slowly to a solution of 3 g (6.17 mmol) of tert-butyl 4-(2-{[tert-butyldiphenylsilyl]oxy}ethyl)-4-fluoro-1-piperidinecarboxylate, obtained in step 12.3, in 20 ml of dichloromethane. Stirring is continued at room temperature for 5 hours. The reaction mixture is poured into a mixture of ice-water and 28% aqueous ammonia. The phases are separated by settling, the aqueous phase is extracted twice with dichloromethane and the combined organic phases are washed with saturated aqueous sodium chloride solution, dried over sodium sulfate and concentrated under reduced pressure.

2.30 g of product are obtained in the form of a yellow oil, which is used without further purification in the following step.

12.5. 2-[4-(2-{[tert-butyldiphenylsilyl]oxy}ethyl)-4-fluoro-1-piperidyl]quinoline The process is performed as described in Example 2 (step 2.1). Starting with 1.18 g (5.68 mmol) of 2-bromoquinoline (Eur. J. Org. Chem. 2002, 4181-4184), 2.30 g (5.98 mmol) of 4-(2-{[tert-butyl(diphenyl)silyl]oxy}ethyl)-4-fluoropiperidine, obtained in step 12.4, 0.66 g (6.81 mmol) of sodium tert-butoxide, 0.149 g (0.239 mmol) of BINAP and 0.074 g (0.081 mmol) of tris(dibenzylideneacetone)dipalladium, and after chromatography on silica gel, eluting with a 10/90 mixture of ethyl acetate and cyclohexane, 2.15 g of pure product are obtained in the form of an orange-coloured oil.

12.6. 2-[4-Fluoro-1-(2-quinolyl)-4-piperidyl]ethanol 0.40 g (1.26 mmol) of n-tetrabutylammonium fluoride trihydrate is added to a solution of 2.15 g (4.19 mmol) of 2-[4-(2-{[tert-butyldiphenylsilyl]oxy}ethyl)-4-fluoro-1-piperidyl]quinoline, obtained in step 12.5, in 20 ml of tetrahydrofuran. Stirring is continued at room temperature for 4 hours. The mixture is concentrated to dryness and the residue obtained is then purified by chromatography on silica gel, eluting with a 35/65 and then 40/60 mixture of ethyl acetate and cyclohexane.

0.61 g of product is obtained in the form of an orange-coloured oil.

12.7. 2-[4-Fluoro-1-(2-quinolyl)-4-piperidyl]ethyl methanesulfonate

The process is performed as described in Example 3 (step 3.2). Starting with 0.61 g (2.22 mmol) of 2-[4-fluoro-1-(2-quinolyl)-4-piperidyl]ethanol, obtained in step 12.6, 0.280 g (2.45 mmol) of mesyl chloride and 0.35 ml (2.45 mmol) of triethylamine, 0.80 g of product is obtained in the form of an orange-coloured oil, which is used without further purification in the following step.

12.8. 3-{2-[4-Fluoro-1-(2-quinolyl)-4-piperidyl]ethyl}-1,3-oxazolidine-2,4-dione The process is performed according to the method described in Example 3 (step 3.3). Starting with 0.780 g (2.22 mmol) of 2-[4-fluoro-1-(2-quinolyl)-4-piperidyl]ethyl methanesulfonate, obtained in step 12.7, 0.27 g (2.66 mmol) of 1,3-oxazolidine-2,4-dione and 0.51 g (4.43 mmol) of 1,1,3,3-tetramethylguanidine, and after chromatography on silica gel, eluting with a 99/1 mixture of dichloromethane and methanol, 0.520 g of pure product is obtained in the form of a beige-coloured solid.

12.9. 2-(Methylamino)-2-oxoethyl 2-[4-fluoro-1-(2-quinolyl)-4-piperidyl]ethylcarbamate The process is performed according to the procedure described in Example 1 (step 1.5). Starting with 0.52 g (1.46 mmol) of 3-{2-[4-fluoro-1-(2-quinolyl)-4-piperidyl]ethyl}-1,3-oxazolidine-2,4-dione, obtained in step 12.8, and 3.6 ml (7.28 mmol) of a solution (2M) of methylamine in tetrahydrofuran, and after chromatography on silica gel, eluting with a 99/1 mixture of ethyl acetate and methanol, followed by crystallization from diethyl ether, 0.390 g of pure product is obtained in the form of a white solid.

LC-MS: M+H=389 m.p. (° C.): 147-149° C. $^1$H NMR (CDCl$_3$) δ (ppm): 1.70-2.10 (unresolved peak, 6H); 2.90 (d, 3H); 3.40 (broad t, 2H); 3.50 (q, 2H); 4.40 (broad d, 2H); 4.60 (s, 2H); 5.15 (broad s, 1H); 6.15 (broad s, 1H); 7.05 (d, 1H); 7.25 (t, 1H); 7.55 (t, 1H); 7.65 (d, 1H); 7.75 (d, 1H); 7.95 (d, 1H).

EXAMPLE 13

Compound 49

2-(Methylamino)-2-oxoethyl 2-[1-(6-isobutyl-2-pyridyl)-4-piperidyl]ethylcarbamate

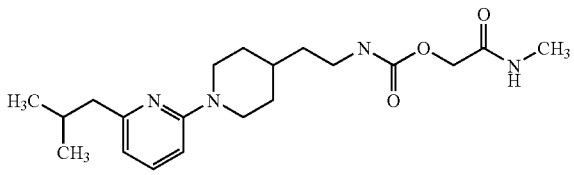

13.1. 2-[1-(6-Bromo-2-pyridyl)-4-piperidyl]ethanol

The process is performed as described in Example 4 (step 4.1). Starting with 30.20 g (127 mmol) of 2,6-dibromopyridine and 16.45 g (127 mmol) of 2-(4-piperidyl)ethanol, and after chromatography on silica gel, eluting with a 30/70 mixture of ethyl acetate and cyclohexane, 7 g of pure product are obtained in the form of an oil.

13.2. 2-[1-(6-Bromo-2-pyridyl)-4-piperidyl]ethyl methanesulfonate

The process is performed as described in Example 3 (step 3.2). Starting with 7 g (24.50 mmol) of 2-[1-(6-bromo-2-pyridyl)-4-piperidyl]ethanol, obtained in step 13.1, 2.50 ml (26.90 mmol) of mesyl chloride and 3.80 ml (26.90 mmol) of triethylamine, 8.68 g of product are obtained in the form of an oil, which is used without further purification in the following step.

13.3. 3-{2-[1-(6-Bromo-2-pyridyl)-4-piperidyl]ethyl}-1,3-oxazolidine-2,4-dione The process is performed according to the method described in Example 3 (step 3.3). Starting with 8.68 g (23.80 mmol) of 2-[1-(6-bromo-2-pyridyl)-4-piperidyl]ethyl methanesulfonate, obtained in step 13.2, 2.90 g (28.60 mmol) of 1,3-oxazolidine-2,4-dione and 6 ml (47.60 mmol) of 1,1,3,3-tetramethylguanidine, and after chromatography on silica gel, eluting with a 97/3 mixture of dichloromethane and methanol, 4.52 g of product are obtained in the form of an oil.

13.4. 3-{2-[1-(6-Isobutyl-2-pyridyl)-4-piperidyl]ethyl}-1,3-oxazolidine-2,4-dione 2 g (5.43 mmol) of 3-{2-[1-(6-bromo-2-pyridyl)-4-piperidyl]ethyl}-1,3-oxazolidine-2,4-dione, prepared in step 13.3, and 0.20 g (0.271 mmol) of dichlorobis(triphenylphosphine)palladium (Pd(PPh$_3$)$_2$Cl$_2$) suspended in 10 ml of tetrahydrofuran are introduced under an inert atmosphere. 22 ml (10.80 mmol) of a solution (0.5 M) of bromo(isobutyl)zinc in tetrahydrofuran are then added. Stirring is continued at room temperature for 17 hours. The reaction mixture is poured into water and ethyl acetate. The phases are separated by settling, the aqueous phase is extracted twice with ethyl acetate, the combined organic phases are dried over sodium sulfate and the filtrate is concentrated under reduced pressure. The residue thus obtained is purified by chromatography on silica gel, eluting with a 20/80 mixture of ethyl acetate and cyclohexane.

1.41 g of product are obtained in the form of a white solid. m.p. (° C.): 94-96° C.

13.5. 2-(Methylamino)-2-oxoethyl 2-[1-(6-isobutyl-2-pyridyl)-4-piperidyl]ethylcarbamate The process is performed according to the procedure described in Example 1 (step 1.5). Starting with 0.72 g (2.08 mmol) of 3-{2-[1-(6-isobutyl-2-pyridyl)-4-piperidyl]ethyl}-1,3-oxazolidine-2,4-dione, obtained in step 13.4, and 5.20 ml (10.40 mmol) of a solution (2M) of methylamine in tetrahydrofuran, and after chromatography on silica gel, eluting with a 95/5/0.5 mixture of dichloromethane, methanol and 28% aqueous ammonia, followed by crystallization from diisopropyl ether, 0.540 g of pure product is obtained in the form of a white solid.

LC-MS: M+H=377 m.p. (° C.): 97-99° C. $^1$H NMR (DMSO) δ (ppm): 0.85 (d, 6H); 1.05 (m, 2H); 1.20-1.60 (unresolved peak, 3H); 1.70 (broad d, 2H); 2.0 (m, 1H); 2.40 (d, 2H); 2.55 (d, 3H); 2.70 (broad t, 2H); 3.05 (broad q, 2H); 4.20 (broad d, 2H); 4.30 (s, 2H); 6.35 (d, 1H); 6.55 (d, 1H); 7.15 (broad t, 1H); 7.40 (dd, 1H); 7.75 (broad s, 1H).

EXAMPLE 14

Compound 58

2-Amino-2-oxoethyl 2-[1-(6-phenyl-2-pyridyl)-4-piperidyl]methylcarbamate

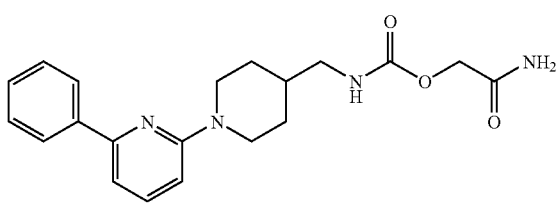

14.1. 3-{2-[1-(6-Phenyl-2-pyridyl)-4-piperidyl]methyl}-1,3-oxazolidine-2,4-dione 0.20 g (0.56 mmol) of 3-{2-[1-(6-bromo-2-pyridyl)-4-piperidyl]methyl}-1,3-oxazolidine-2,4-dione, prepared according to the procedure described in Example 13 (steps 13.1, 13.2 and 13.3), 0.089 g (0.73 mmol) of phenylboronic acid and 0.480 g (2.25 mmol) of hydrated potassium phosphate suspended in 3 ml of 1,2-dimethoxyethane are introduced under an inert atmosphere. 0.040 g (0.0346 mmol) of tetrakis(triphenylphosphine)palladium is then added. The reaction mixture is then maintained at about 85° C. for 16 hours. The resulting mixture is concentrated under reduced pressure. The residue is taken up in ethyl acetate and water, the aqueous phase is separated out and extracted twice with ethyl acetate, the combined organic phases are dried over sodium sulfate and the filtrate is concentrated under reduced pressure. The residue thus obtained is purified by chromatography on silica gel, eluting with a 40/60 mixture of ethyl acetate and cyclohexane.

0.175 g of product is obtained.

14.2. 2-Amino-2-oxoethyl 2-[1-(6-phenyl-2-pyridyl)-4-piperidyl]methylcarbamate The process is performed according to the procedure described in Example 3 (step 3.4). Starting with 0.175 g (0.499 mmol) of 3-{2-[1-(6-phenyl-2-pyridyl)-4-piperidyl]methyl}-1,3-oxazolidine-2,4-dione, obtained in step 14.1, and 2.5 ml (17.45 mmol) of a solution (7M) of aqueous ammonia in methanol, 0.070 g of pure product is obtained in the form of a white solid, after crystallization from ethyl acetate.

LC-MS: M+H=369 m.p. (° C.): 131-132° C. $^1$H NMR (CDCl$_3$) δ (ppm): 1.20-1.90 (unresolved peak, 5H); 2.90 (broad t, 2H); 3.20 (t, 2H); 4.50 (broad d, 2H); 4.60 (s, 2H); 5.0 (broad s, 1H); 5.55 (broad s, 1H); 6.15 (broad s, 1H); 6.65 (d, 1H); 7.10 (d, 1H); 7.35-7.60 (m, 4H); 8.15 (dd, 2H).

EXAMPLE 15

Compound 130

2-(Methylamino)-2-oxoethyl 2-[1-(5-chloro-2-quinolyl)-4-piperidyl]ethylcarbamate

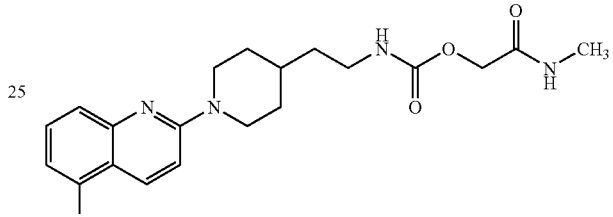

15.1. 2-[1-(5-Chloro-2-quinolyl)-4-piperidyl]ethanol

The process is performed as described in Example 4 (step 4.1). Starting with 4.78 g (24.14 mmol) of 2-chloro-5-chloroquinoline (J. Med. Chem., 2002, 45, 3130-3137) and 3.43 g (26.55 mmol) of 2-(4-piperidyl)ethanol, 7 g of product are obtained in the form of an oil, which is used without further purification in the following step.

15.2. 2-[1-(5-Chloro-2-quinolyl)-4-piperidyl]ethyl methanesulfonate

The process is performed as described in Example 3 (step 3.2). Starting with 7 g (24.07 mmol) of 2-[1-(5-chloro-2-quinolyl)-4-piperidyl]ethanol, obtained in step 15.1, 3.31 g (28.89 mmol) of mesyl chloride and 5.10 ml (36.11 mmol) of triethylamine, 8.70 g of product are obtained in the form of an oil, which is used without further purification in the following step.

15.3. 3-{2-[1-(5-Chloro-2-quinolyl)-4-piperidyl]ethyl}-1,3-oxazolidine-2,4-dione The process is performed according to the method described in Example 3 (step 3.3). Starting with 8.7 g (23.58 mmol) of 2-[1-(5-chloro-2-quinolyl)-4-piperidyl]ethyl methanesulfonate, obtained in step 15.2, 2.86 g (28.30 mmol) of 1,3-oxazolidine-2,4-dione and 5.43 g (47.17 mmol) of 1,1,3,3-tetramethyl-guanidine, and after chromatography on silica gel, eluting with a 99.5/0.5 mixture of dichloromethane and methanol, 6.40 g of product are obtained in the form of a white solid.

m.p. (° C.): 136° C.

15.4. 2-(Methylamino)-2-oxoethyl 2-[1-(5-chloro-2-quinolyl)-4-piperidyl]ethylcarbamate The process is performed according to the procedure described in Example 1 (step 1.5). Starting with 6.40 g (17.12 mmol) of 3-{2-[1-(5-chloro-2-quinolyl)-4-piperidyl]ethyl}-1,3-oxazolidine-2,4-dione, obtained in step 15.3, and 60 ml (119.84 mmol) of a solution (2M) of methylamine in tetrahydrofuran, and after chromatography on silica gel, eluting with a 98/2 and then 96/4 mixture of dichloromethane and methanol, followed by crystallization from diisopropyl ether, 5.14 g of product are obtained in the form of a white solid.

LC-MS: M+H=405 m.p. (° C.): 158-162° C. $^1$H NMR (CDCl$_3$) δ (ppm): 1.10-1.80 (unresolved peak, 5H); 1.9 (broad d, 2H); 2.90 (d, 3H); 3.0 (m, 2H); 3.30 (q, 2H); 4.60 (m, 4H); 4.85 (broad s, 1H); 6.10 (broad s, 1H); 7.05 (d, 1H); 7.25 (d, 1H); 7.40 (dd, 1H); 7.60 (d, 1H); 8.30 (s, 1H).

Table 1 below illustrates the chemical structures and physical properties of a number of compounds according to the invention.

In this table:
- in the "base or salt" column, "base" represents a compound in free base form, whereas "HCl" represents a compound in hydrochloride form;
- OMe represents a methoxy group.

TABLE 1

(I)

| No | R$_1$ | m | n | A | B | R$_3$ | base or salt | m.p.(° C.) |
|---|---|---|---|---|---|---|---|---|
| 1. | phenyl | 2 | 2 | N | (CH$_2$)$_3$ | CH$_2$CONHCH$_3$ | base | 131 |
| 2. | 3-Cl-phenyl-pyridyl | 2 | 2 | N | (CH$_2$)$_2$ | CH$_2$CONH$_2$ | base | 417* |
| 3. | 3-Cl-phenyl-pyridyl | 2 | 2 | N | (CH$_2$)$_2$ | CH$_2$CONHCH$_3$ | base | 165-166 |
| 4. | 4-Cl-phenyl-pyridyl | 2 | 2 | N | (CH$_2$)$_2$ | CH$_2$CONH$_2$ | base | 144-145 |
| 5. | 4-Cl-phenyl-pyridyl | 2 | 2 | N | (CH$_2$)$_2$ | CH$_2$CONHCH$_3$ | base | 138-139 |
| 6. | 3-NC-phenyl-pyridyl | 2 | 2 | N | (CH$_2$)$_2$ | CH$_2$CONH$_2$ | base | 173-174 |
| 7. | 3-NC-phenyl-pyridyl | 2 | 2 | N | (CH$_2$)$_2$ | CH$_2$CONHCH$_3$ | base | 196-197 |
| 8. | 4-NC-phenyl-pyridyl | 2 | 2 | N | (CH$_2$)$_2$ | CH$_2$CONH$_2$ | base | 157-158 |
| 9. | 4-NC-phenyl-pyridyl | 2 | 2 | N | (CH$_2$)$_2$ | CH$_2$CONHCH$_3$ | base | 225-226 |
| 10. | 3-MeO-phenyl-pyridyl | 2 | 2 | N | (CH$_2$)$_2$ | CH$_2$CONH$_2$ | base | 121-122 |
| 11. | 3-MeO-phenyl-pyridyl | 2 | 2 | N | (CH$_2$)$_2$ | CH$_2$CONHCH$_3$ | base | 141-142 |

TABLE 1-continued
(I)
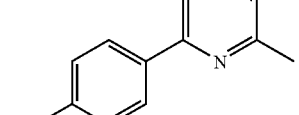
| No | R₁ | m | n | A | B | R₃ | base or salt | m.p.(° C.) |
|---|---|---|---|---|---|---|---|---|
| 12. | 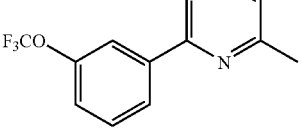 | 2 | 2 | N | (CH₂)₂ | CH₂CONH₂ | base | 139-140 |
| 13. | | 2 | 2 | N | (CH₂)₂ | CH₂CONHCH₃ | base | 170-171 |
| 14. | 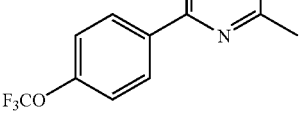 | 2 | 2 | N | (CH₂)₂ | CH₂CONH₂ | base | 128-129 |
| 15. | | 2 | 2 | N | (CH₂)₂ | CH₂CONHCH₃ | base | 153-154 |
| 16. | 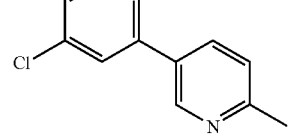 | 2 | 2 | N | (CH₂)₂ | CH₂CONH₂ | base | 160-161 |
| 17. | | 2 | 2 | N | (CH₂)₂ | CH₂CONHCH₃ | base | 148-149 |
| 18. | 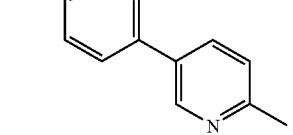 | 2 | 2 | N | (CH₂)₂ | CH₂CONH₂ | base | 156-157 |
| 19. | | 2 | 2 | N | (CH₂)₂ | CH₂CONHCH₃ | base | 157-158 |
| 20. | 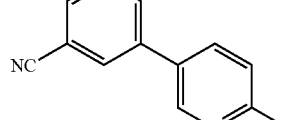 | 2 | 2 | N | (CH₂)₂ | CH₂CONH₂ | base | 178-179 |
| 21. | | 2 | 2 | N | (CH₂)₂ | CH₂CONHCH₃ | base | 432* |
| 22. | 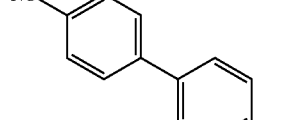 | 2 | 2 | N | (CH₂)₂ | CH₂CONH₂ | base | 158-159 |
| 23. | | 2 | 2 | N | (CH₂)₂ | CH₂CONHCH₃ | base | 180-181 |
| 24. |  | 2 | 2 | N | (CH₂)₂ | CH₂CONH₂ | base | 185-186 |
| 25. | | 2 | 2 | N | (CH₂)₂ | CH₂CONHCH₃ | base | 193-194 |

TABLE 1-continued
(I)
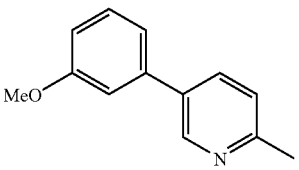
| No | R₁ | m | n | A | B | R₃ | base or salt | m.p.(° C.) |
|---|---|---|---|---|---|---|---|---|
| 26. | 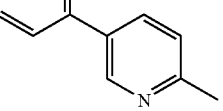 | 2 | 2 | N | (CH₂)₂ | CH₂CONH₂ | base | 153-154 |
| 27. |  | 2 | 2 | N | (CH₂)₂ | CH₂CONHCH₃ | base | 125-126 |
| 28. | MeO- | 2 | 2 | N | (CH₂)₂ | CH₂CONH₂ | base | 193-194 |
| 29. | 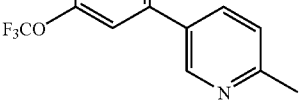 | 2 | 2 | N | (CH₂)₂ | CH₂CONHCH₃ | base | 176-177 |
| 30. | 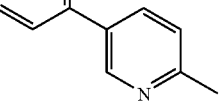 | 2 | 2 | N | (CH₂)₂ | CH₂CONH₂ | base | 160-161 |
| 31. |  | 2 | 2 | N | (CH₂)₂ | CH₂CONHCH₃ | base | 156-157 |
| 32. | F₃CO- | 2 | 2 | N | (CH₂)₂ | CH₂CONH₂ | base | 189-190 |
| 33. |  | 2 | 2 | N | (CH₂)₂ | CH₂CONHCH₃ | base | 196-197 |
| 34. | O₂N- | 2 | 3 | N | (CH₂)₃ | CH₂CONHCH₃ | base | 100 (dec.) |
| 35. | F₃C- -Cl | 2 | 3 | N | (CH₂)₃ | CH₂CONHCH₃ | HCl | 451* |
| 36. | CF₃ | 2 | 3 | N | (CH₂)₃ | CH₂CONHCH₃ | HCl | 172-174 |
| 37. | 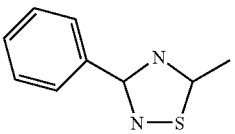 | 2 | 3 | N | (CH₂)₃ | CH₂CONHCH₃ | base | 118-122 |

TABLE 1-continued

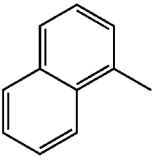

(I)

| No | R₁ | m | n | A | B | R₃ | base or salt | m.p.(° C.) |
|---|---|---|---|---|---|---|---|---|
| 38. |  | 2 | 2 | N | $(CH_2)_2$ | $CH_2CONHCH_3$ | HCl | 166 |
| 39. | | 2 | 2 | N | $(CH_2)_3$ | $CH_2CONHCH_2$ | HCl | 167 |
| 40. | 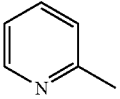 | 1 | 1 | CH | $CH_2$ | $CH_2CONH_2$ | base | 149-151 |
| 41. | | 1 | 1 | CH | $CH_2$ | $CH_2CONHCH_3$ | base | 137-139 |
| 42. | | 1 | 1 | CH | $CH_2$ | $CH_2CONHCH_2$ (cyclopropyl) | base | 119-121 |
| 43. | | 2 | 3 | CH | $(CH_2)_2$ | $CH_2CONHCH_3$ | base | 110-112 |
| 44. | | 2 | 2 | CH | $(CH_2)_2$ | $CH_2CONH_2$ | base | 140-142 |
| 45. | | 2 | 2 | | $(CH_2)_2$ | $CH_2CONHCH_3$ | base | 127-129 |
| 46. | 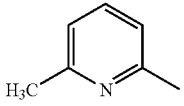 | 2 | 2 | CH | $(CH_2)_2$ | $CH_2CONHCH_3$ | HCl | 168-170 |
| 47. | 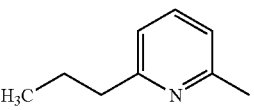 | 2 | 2 | CH | $(CH_2)_2$ | $CH_2CONHCH_3$ | HCl | 95-100 |
| 48. | 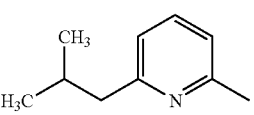 | 2 | 2 | CH | $(CH_2)_2$ | $CH_2CONHCH_3$ | base | 113-115 |
| 49. | 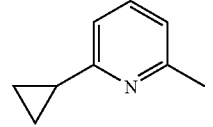 | 2 | 2 | CH | $(CH_2)_2$ | $CH_2CONHCH_3$ | base | 97-99 |
| 50. | | 2 | 2 | CH | $(CH_2)_2$ | $CH_2CONH_2$ | base | 107-109 |
| 51. | 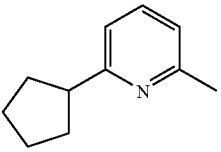 | 2 | 2 | CH | $(CH_2)_2$ | $CH_2CONHCH_3$ | base | 108-110 |
| 52. | 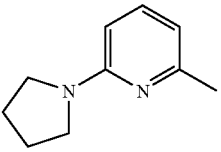 | 2 | 2 | CH | $(CH_2)_2$ | $CH_2CONHCH_3$ | base | 98-100 |
| 53. |  | 2 | 2 | CH | $(CH_2)_2$ | $CH_2CONHCH_3$ | base | 123-125 |

TABLE 1-continued

Structure (I): R1-(CH2)m-A(-(CH2)n-)-B-NH-C(=O)-O-R3

| No | R1 | m | n | A | B | R3 | base or salt | m.p.(° C.) |
|---|---|---|---|---|---|---|---|---|
| 54. | 6-bromo-2-methylpyridin-yl | 2 | 2 | CH | — | CH2CONH2 | base | 169 |
| 55. | | 2 | 2 | CH | CH2 | CH2CONH2 | base | 148-149 |
| 56. | | 2 | 2 | CH | (CH2)2 | CH2CONH2 | base | 131-132 |
| 57. | 6-phenyl-2-methylpyridin-yl | 2 | 2 | CH | — | CH2CONH2 | base | 153 |
| 58. | | 2 | 2 | CH | CH2 | CH2CONH2 | base | 131-132 |
| 59. | | 2 | 2 | CH | (CH2)2 | CH2CONH2 | base | 116-117 |
| 60. | 6-(4-fluorophenyl)-2-methylpyridin-yl | 2 | 2 | CH | — | CH2CONH2 | base | 190-191 |
| 61. | | 2 | 2 | CH | CH2 | CH2CONH2 | base | 155-156 |
| 62. | | 2 | 2 | CH | (CH2)2 | CH2CONH2 | base | 155-156 |
| 63. | 3-bromo-2-methylpyridin-yl | 2 | 2 | CH | — | CH2CONH2 | base | 159-160 |
| 64. | | 2 | 2 | CH | CH2 | CH2CONH2 | base | 132 |
| 65. | | 2 | 2 | CH | (CH2)2 | CH2CONH2 | base | 134-135 |
| 66. | 3-cyano-2-methylpyridin-yl | 2 | 2 | CH | CH2 | CH2CONH2 | base | 146-147 |
| 67. | | 2 | 2 | CH | (CH2)2 | CH2CONH2 | base | 332* |
| 68. | 3-phenyl-2-methylpyridin-yl | 2 | 2 | CH | — | CH2CONH2 | base | 131-132 |
| 69. | | 2 | 2 | CH | CH2 | CH2CONH2 | base | 129-130 |
| 70. | | 2 | 2 | CH | (CH2)2 | CH2CONH2 | base | 86-87 |
| 71. | 3-(4-fluorophenyl)-2-methylpyridin-yl | 2 | 2 | CH | — | CH2CONH2 | base | 58-59 |
| 72. | | 2 | 2 | CH | CH2 | CH2CONH2 | base | 387 |
| 73. | | 2 | 2 | CH | (CH2)2 | CH2CONH2 | base | 58-59 |
| 74. | 4-trifluoromethyl-2-methylpyridin-yl | 2 | 2 | CH | CH2 | CH2CONH2 | base | 152-153 |
| 75. | | 2 | 2 | CH | (CH2)2 | CH2CONH2 | base | 163 |

TABLE 1-continued

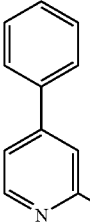

(I)

| No | R₁ | m | n | A | B | R₃ | base or salt | m.p.(° C.) |
|---|---|---|---|---|---|---|---|---|
| 76. | 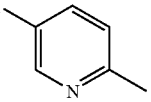 | 2 | 2 | CH | (CH₂)₂ | CH₂CONHCH₃ | base | 121-123 |
| 77. | | 2 | 2 | CH | (CH₂)₂ | CH₂CONH₂ | base | 137-139 |
| 78. | 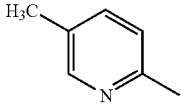 | 2 | 2 | CH | CH₂ | CH₂CONH₂ | base | 327* |
| 79. | | 2 | 2 | CH | (CH₂)₂ | CH₂CONH₂ | base | 162-163 |
| 80. | 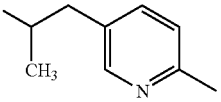 | 2 | 2 | CH | — | CH₂CONH₂ | base | 168 |
| 81. | | 2 | 2 | CH | CH₂ | CH₂CONH₂ | base | 176 |
| 82. | | 2 | 2 | CH | (CH₂)₂ | CH₂CONH₂ | base | 174-175 |
| 83. | 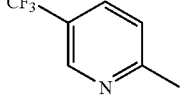 | 2 | 2 | CH | CH₂ | CH₂CONH₂ | base | 169-170 |
| 84. | | 2 | 2 | CH | (CH₂)₂ | CH₂CONH₂ | base | 145-146 |
| 85. | 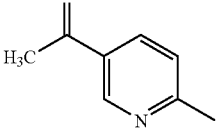 | 2 | 2 | CH | (CH₂)₂ | CH₂CONH₂ | base | 119-121 |
| 86. | | 2 | 2 | CH | (CH₂)₂ | CH₂CONHCH₃ | base | 109-111 |
| 87. | 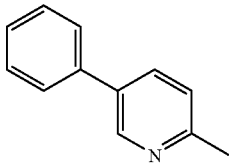 | 2 | 2 | CH | CH₂ | CH₂CONH₂ | base | 169-170 |
| 88. | | 2 | 2 | CH | (CH₂)₂ | CH₂CONH₂ | base | 164-165 |
| 89. |  | 2 | 2 | CH | CH₂ | CH₂CONH₂ | base | 174-175 |
| 90. |  | 2 | 2 | CH | CH₂ | CH₂CONH₂ | base | 162-163 |
| 91. | | 2 | 2 | CH | (CH₂)₂ | CH₂CONH₂ | base | 151-152 |
| 92. |  | 2 | 2 | CH | — | CH₂CONH₂ | base | 195-196 |
| 93. | | 2 | 2 | CH | CH₂ | CH₂CONH₂ | base | 229-230 |

TABLE 1-continued (I)

R1-[cyclobutane ring with (CH2)m and (CH2)n]-A-B-NH-C(=O)-O-R3

| No | R1 | m | n | A | B | R3 | base or salt | m.p.(° C.) |
|---|---|---|---|---|---|---|---|---|
| 94. | 4-F-phenyl-(6-methylpyridin-3-yl) | 2 | 2 | CH | | CH$_2$CONH$_2$ | base | 194-195 |
| 95. | 4-F-phenyl-(6-methylpyridin-3-yl) | 2 | 2 | CH | CH$_2$ | CH$_2$CONH$_2$ | base | 222-223 |
| 96. | 4-F-phenyl-(6-methylpyridin-3-yl) | 2 | 2 | CH | (CH$_2$)$_2$ | CH$_2$CONH$_2$ | base | 182 |
| 97. | 4-Cl-phenyl-(6-methylpyridin-3-yl) | 2 | 2 | CH | (CH$_2$)$_2$ | CH$_2$CONH$_2$ | base | 196-199 |
| 98. | 4-Cl-phenyl-(6-methylpyridin-3-yl) | 2 | 2 | CH | (CH$_2$)$_2$ | CH$_2$CONHCH$_3$ | base | 161-163 |
| 99. | 5-ethyl-2-methylpyrimidin-5-yl | 2 | 2 | CH | CH$_2$ | CH$_2$CONH$_2$ | base | 157-158 |
| 100. | 5-ethyl-2-methylpyrimidin-5-yl | 2 | 2 | CH | (CH$_2$)$_2$ | CH$_2$CONH$_2$ | base | 175-176 |
| 101. | 5-propyl-2-methylpyrimidin-5-yl | 2 | 2 | CH | CH$_2$ | CH$_2$CONH$_2$ | base | 163-164 |
| 102. | 5-(4-Cl-phenyl)-2-methylpyrimidin-5-yl | 2 | 2 | CH | (CH$_2$)$_2$ | CH$_2$CONH$_2$ | base | 418* |
| 103. | 4-CF$_3$-2-methylpyrimidin-5-yl | 2 | 2 | CH | CH$_2$ | CH$_2$CONH$_2$ | base | 190-191 |
| 104. | 4-(N,N-dimethylamino)-2,6-dimethylpyrimidin-5-yl | 2 | 2 | CH | (CH$_2$)$_2$ | CH$_2$CONH$_2$ | base | 165-166 |
| 105. | 2-amino-4,6-dimethylpyrimidin-5-yl | 2 | 2 | CH | CH$_2$ | CH$_2$CONH$_2$ | base | 323* |
| 106. | 2-amino-4,6-dimethylpyrimidin-5-yl | 2 | 2 | CH | (CH$_2$)$_2$ | CH$_2$CONH$_2$ | base | 202-203 |

TABLE 1-continued (I)

| No | R₁ | m | n | A | B | R₃ | base or salt | m.p.(° C.) |
|---|---|---|---|---|---|---|---|---|
| 107. | 4,6-dimethyl-2-(pyridin-2-yl)pyrimidinyl | 2 | 2 | CH | CH₂ | CH₂CONH₂ | base | 172-173 |
| 108. | 6-phenylpyrimidin-4-yl | 2 | 2 | CH | CH₂ | CH₂CONH₂ | base | 370* |
| 109. | 2-methyl-6-phenylpyrimidin-4-yl (isomer) | 2 | 2 | CH | CH₂ | CH₂CONH₂ | base | 177-178 |
| 110. | 6-(imidazol-1-yl)pyrimidin-4-yl | 2 | 2 | CH | CH₂ | CH₂CONH₂ | base | 202-203 |
| 111. | 6-(imidazol-1-yl)pyrimidin-4-yl | 2 | 2 | CH | (CH₂)₂ | CH₂CONH₂ | base | 185-186 |
| 112. | pyrazinyl | 2 | 2 | CH | CH₂ | CH₂CONH₂ | base | 165-166 |
| 113. | pyrazinyl | 2 | 2 | CH | (CH₂)₂ | CH₂CONH₂ | base | 126-127 |
| 114. | 2-amino-6-methylpyrimidin-4-yl | 2 | 2 | CH | CH₂ | CH₂CONH₂ | base | 309* |
| 115. | 2-amino-6-methylpyrimidin-4-yl | 2 | 2 | CH | (CH₂)₂ | CH₂CONH₂ | base | 159-160 |
| 116. | 3,5,6-trimethylpyrazin-2-yl | 2 | 2 | CH | CH₂ | CH₂CONH₂ | base | 161-162 |
| 117. | 3,5,6-trimethylpyrazin-2-yl | 2 | 2 | CH | (CH₂)₂ | CH₂CONH₂ | base | 126-127 |

TABLE 1-continued

(I)

| No | R₁ | m | n | A | B | R₃ | base or salt | m.p.(° C.) |
|---|---|---|---|---|---|---|---|---|
| 118. |  | 2 | 2 | CH | CH₂ | CH₂CONH₂ | base | 158-159 |
| 119. | | 2 | 2 | CH | (CH₂)₂ | CH₂CONH₂ | base | 174-175 |
| 120. | 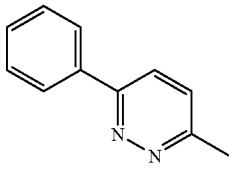 | 2 | 2 | CH | (CH₂)₂ | CH₂CONH₂ | base | 204-205 |
| 121. | 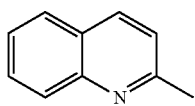 | 2 | 2 | CH | CH₂ | CH₂CONH₂ | base | 229-230 |
| 122. | | 2 | 2 | CH | (CH₂)₂ | CH₂CONH₂ | base | 228-229 |
| 123. | 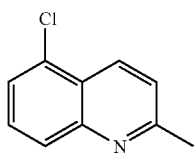 | 2 | 2 | CH | CH₂ | CH₂CONHCH₃ | base | 153-157 |
| 124. | | 2 | 2 | CH | CH₂ | CH₂CONH₂ | base | 206-212 |
| 125. | | 2 | 2 | CH | CH₂ | CH(CH₃)CONHCH₃ | base | 129-130 |
| 126. | | 2 | 2 | CH | (CH₂)₂ | CH₂CONHCH₃ | base | 126-128 |
| 127. | | 2 | 2 | CH | (CH₂)₂ | CH₂CONH₂ | base | 135-137 |
| 128. | | 2 | 2 | CF | (CH₂)₂ | CH₂CONHCH₃ | base | 147-149 |
| 129. | | 2 | 2 | C(OH) | (CH₂)₂ | CH₂CONHCH₃ | base | 82-90 |
| 130. | 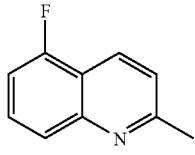 | 2 | 2 | CH | (CH₂)₂ | CH₂CONHCH₃ | base | 158-162 |
| 131. | | 2 | 2 | CH | (CH₂)₂ | CH₂CONH₂ | base | 171-175 |
| 132. | 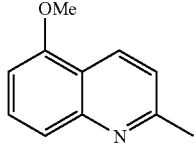 | 2 | 2 | CH | (CH₂)₂ | CH₂CONHCH₃ | base | 162-163 |
| 133. | 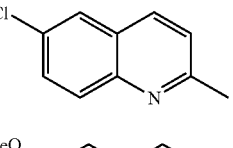 | 2 | 2 | CH | (CH₂)₂ | CH₂CONHCH₃ | base | 154-156 |
| 134. | 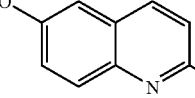 | 2 | 2 | CH | CH₂ | CH₂CONHCH₃ | base | 147-151 |
| 135. | | 2 | 2 | CH | CH₂ | CH₂CONH₂ | base | 207-208 |
| 136. | | 2 | 2 | CH | (CH₂)₂ | CH₂CONHCH₃ | base | 155-157 |
| 137. | | 2 | 2 | CH | (CH₂)₂ | CH₂CONH₂ | base | 189-191 |
| 138. | MeO (quinoline) | 2 | 2 | CH | (CH₂)₂ | CH₂CONH₂ | base | 163-165 |
| 139. | | 2 | 2 | CH | (CH₂)₂ | CH₂CONHCH₃ | base | 135-137 |
| 140. | | 2 | 2 | CH | (CH₂)₂ | CH₂CONHCH₂CH₃ | base | 114-116 |
| 141. | | 2 | 2 | CH | (CH₂)₂ | CH₂CONHCH₂ (cyclopropyl) | base | 95-100 |

TABLE 1-continued

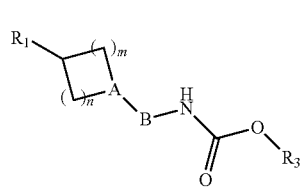
(I)

| No | R₁ | m | n | A | B | R₃ | base or salt | m.p.(° C.) |
|---|---|---|---|---|---|---|---|---|
| 142. | 7-Cl-2-methylquinolin-3-yl | 2 | 2 | CH | (CH₂)₂ | CH₂CONH₂ | base | 191-193 |
| 143. | | 2 | 2 | CH | (CH₂)₂ | CH₂CONHCH₃ | base | 149-151 |
| 144. | 8-Cl-2-methylquinolin-3-yl | 2 | 2 | CH | (CH₂)₂ | CH₂CONHCH₃ | base | 146-150 |
| 145. | | 2 | 2 | CH | (CH₂)₂ | CH₂CONH₂ | base | 171-173 |
| 146. | 3-methylquinolin-yl | 2 | 2 | CH | (CH₂)₂ | CH₂CONHCH₃ | base | 140-142 |
| 147. | | 2 | 2 | CH | (CH₂)₂ | CH₂CONH₂ | base | 160-162 |
| 148. | 4-methylquinolin-yl | 2 | 2 | CH | (CH₂)₂ | CH₂CONHCH₃ | HCl | 148-150 |
| 149. | | 2 | 2 | CH | (CH₂)₂ | CH₂CONH₂ | HCl | 218-221 |
| 150. | 2-methyl-1,5-naphthyridin-3-yl | 2 | 2 | CH | (CH₂)₂ | CH₂CONHCH₂ | base | 130-132 |
| 151. | 1-methylisoquinolin-yl | 1 | 2 | CH | CH₂ | CH₂CONH₂ | base | 109-111 |
| 152. | | 1 | 2 | CH | CH₂ | CH₂CONCH₃ | base | 99-102 |
| 153. | | 2 | 2 | CH | — | CH₂CONCH₃ | HCl | 232-237 |
| 154. | | 2 | 2 | CH | CH₂ | CH₂CONCH₃ | HCl | 208-212 |
| 155. | | 2 | 2 | CH | (CH₂)₂ | CH₂CONCH₃ | HCl | 132-136 |
| 156. | | 2 | 2 | CH | (CH₂)₂ | CH₂CONH₂ | HCl | 120-124 |
| 157. | | 2 | 2 | CH | (CH₂)₃ | CH₂CONCH₃ | HCl | 385* |
| 158. | 6-F-1-methylisoquinolin-yl | 2 | 2 | CH | (CH₂)₂ | CH₂CONHCH₂ | base | 135-139 |
| 159. | | 2 | 2 | CH | (CH₂)₂ | CH₂CONHCH₃ | base | 144-148 |
| 160. | 6-Cl-1-methylisoquinolin-yl | 2 | 2 | CH | (CH₂)₂ | CH₂CONHCH₃ | base | 134-136 |

TABLE 1-continued
(I)
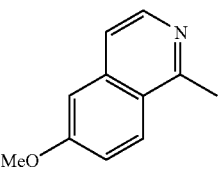
| No | R₁ | m | n | A | B | R₃ | base or salt | m.p.(° C.) |
|---|---|---|---|---|---|---|---|---|
| 161. | 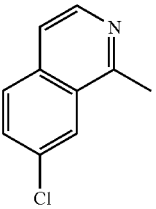 | 2 | 2 | CH | CH₂ | CH₂CONHCH₃ | HCl | 387* |
| 162. | | 2 | 2 | CH | (CH₂)₂ | CH₂CONHCH₃ | base | 100-104 |
| 163. | | 2 | 2 | CH | (CH₂)₂ | CH₂CONH₂ | base | 118-120 |
| 164. | 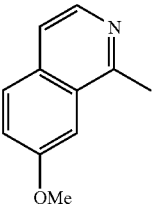 | 2 | 2 | CH | (CH₂)₂ | CH₂CONHCH₃ | HCl | 186-188 |
| 165. | 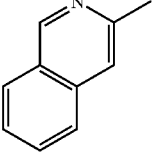 | 2 | 2 | CH | (CH₂)₂ | CH₂CONHCH₃ | base | 80-86 |
| 166. | 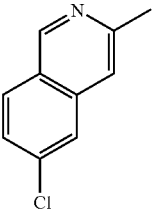 | 2 | 2 | CH | (CH₂)₂ | CH₂CONHCH₃ | base | 156-158 |
| 167. | | 2 | 2 | CH | (CH₂)₂ | CH₂CONH₂ | base | 176-178 |
| 168. | 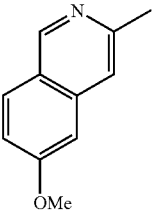 | 2 | 2 | CH | (CH₂)₂ | CH₂CONHCH₃ | base | 148-150 |
| 169. | | 2 | 2 | CH | (CH₂)₂ | CH₂CONHCH₃ | base | 154-156 |

TABLE 1-continued

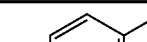

(I)

| No | R₁ | m | n | A | B | R₃ | base or salt | m.p.(° C.) |
|---|---|---|---|---|---|---|---|---|
| 170. | 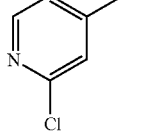 | 2 | 2 | CH | (CH₂)₂ | CH₂CONH₂ | base | 156-158 |
| 171. | | 2 | 2 | CH | (CH₂)₂ | CH₂CONHCH₃ | base | 156-158 |
| 172. | 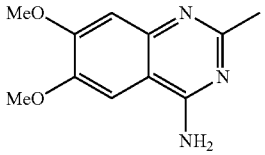 | 2 | 2 | CH | (CH₂)₂ | CH₂CONHCH₃ | HCl | 205-210 |
| 173. | 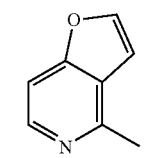 | 2 | 2 | CH | CH₂ | CH₂CONH₂ | base | 419* |
| 174. | | 2 | 2 | CH | (CH₂)₂ | CH₂CONH₂ | base | 105-106 |
| 175. | 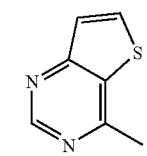 | 2 | 2 | CH | CH₂ | CH₂CONH₂ | base | 129-130 |
| 176. | | 2 | 2 | CH | (CH₂)₂ | CH₂CONH₂ | base | 112-113 |
| 177. | 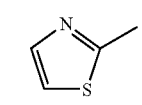 | 2 | 2 | CH | CH₂ | CH₂CONH₂ | base | 180-181 |
| 178. | 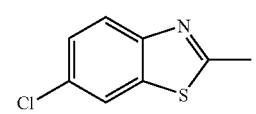 | 2 | 2 | CH | CH₂ | CH₂CONH₂ | base | 244-245 |
| 179. | | 2 | 2 | CH | (CH₂)₂ | CH₂CONHCH₃ | base | 146-150 |
| 180. | | 2 | 2 | CH | (CH₂)₂ | CH₂CONH₂ | base | 169-171 |
| 181. |  | 2 | 2 | CH | CH₂ | CH₂CONH₂ | base | 137-138 |
| 182. | | 2 | 2 | CH | (CH₂)₂ | CH₂CONH₂ | base | 208-209 |
| 183. |  | 2 | 2 | CH | CH₂ | CH₂CONH₂ | base | 183-184 |
| 184. | | 2 | 2 | CH | (CH₂)₂ | CH₂CONH₂ | base | 172-173 |
| 185. |  | 2 | 2 | CH | CH₂ | CH₂CONH₂ | base | 187-188 |
| 186. | | 2 | 2 | CH | (CH₂)₂ | CH₂CONH₂ | base | 191-192 |

TABLE 1-continued

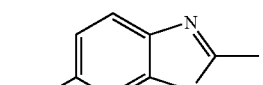

(I)

| No | R₁ | m | n | A | B | R₃ | base or salt | m.p.(° C.) |
|---|---|---|---|---|---|---|---|---|
| 187. | 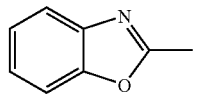 | 2 | 2 | CH | $CH_2$ | $CH_2CONH_2$ | base | 222-223 |
| 188. | 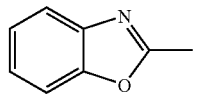 | 2 | 2 | CH | $CH_2$ | $CH_2CONH_2$ | base | 149-150 |
| 189. |  | 2 | 2 | CH | $(CH_2)_2$ | $CH_2CONH_2$ | base | 167-168 |
| 190. | 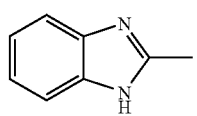 | 2 | 2 | CH | $CH_2$ | $CH_2CONH_2$ | base | 220-221 |
| 191. |  | 2 | 2 | CH | $(CH_2)_2$ | $CH_2CONH_2$ | base | 201-202 |

*M + H (LC-MS)
dec. = decomposition of the product

The compounds of the invention underwent pharmacological trials to determine their inhibitory effect on the enzyme FAAH (Fatty Acid Amide Hydrolase).

The inhibitory activity was demonstrated in a radioenzymatic test based on measuring the product of hydrolysis (ethanolamine [1-³H]) of anandamide [ethanolamine 1-³H] with FAAH (Life Sciences (1995), 56, 1999-2005 and Journal of Pharmacology and Experimented Therapeutics (1997), 283, 729-734). Thus, mouse brains (minus the cerebellum) are removed and stored at −80° C. Membrane homogenates are prepared extemporaneously by homogenizing the tissues using a Polytron blender in 10 mM tris-HCl buffer (pH 8.0) containing 150 mM NaCl and 1 mM EDTA. The enzymatic reaction is then performed in 70 µl of buffer containing fatty-acid-free bovine serum albumin (1 mg/ml). To test compounds at different concentrations, anandamide [ethanolamine 1-³H] (specific activity of 15-20 Ci/mmol) diluted to 10 µM with cold anandamide, and the membrane preparation (400 µg of frozen tissue per test) are successively added. After 15 minutes at 25° C., the enzymatic reaction is quenched by adding 140 µL of chloroform/methanol (2:1). The mixture is stirred for 10 minutes and then centrifuged for 15 minutes at 3500 g. An aliquot (30 µL) of the aqueous phase containing the ethanolamine [1-³H] is counted by liquid scintillation. Under these conditions, the most active compounds of the invention have $IC_{50}$ values (concentration that inhibits 50% of the control enzymatic activity of FAAH) of between 0.001 and 1 µM.

Table 2 below shows the $IC_{50}$ values of a few compounds according to the invention.

TABLE 2

| Compound No. | $IC_{50}$ |
|---|---|
| 47 | 85 µM |
| 126 | 113 µM |
| 166 | 87 µM |

It is thus seen that the compounds according to the invention have inhibitory activity on the enzyme FAAH.

The in vivo activity of the compounds of the invention was evaluated in a test of analgesia.

Thus, the intraperitoneal (i.p.) administration of PBQ (phenylbenzoquinone, 2 mg/kg in 0.9% sodium chloride solution containing 5% ethanol) to male OF1 mice weighing 25 to 30 g, causes abdominal tractions, on average 30 torsions or contractions during the period of 5 to 15 minutes after injection. The test compounds are administered orally or intraperitoneally as a 0.5% suspension in Tween 80, 60 minutes or 120 minutes before the administration of PBQ. Under these conditions, the most powerful compounds of the invention produce a 35% to 70% reduction in the number of tractions induced with PBQ, within a dose range of between 1 and 30 mg/kg.

Table 3 below shows the results of the analgesia test for a few compounds according to the invention.

TABLE 3

| Compound No. | Reduction in the number of tractions (%) |
|---|---|
| 47 | −63% (b) |
| 126 | −43% (b) |
| 166 | −62% (a) |

(a) 1 mg/kg p.o. at 2 hours;
(b) 3 mg/kg p.o. at 1 hour

The enzyme FAAH (Chemistry and Physics of Lipids, (2000), 108, 107-121) catalyses the hydrolysis of the endogenous amide and ester derivatives of various fatty acids such as N-arachidonoylethanolamine (anandamide), N-palmitoylethanolamine, N-oleoylethanolamine, oleamide or 2-arachidonoylglycerol. These derivatives exert different pharmacological activities by interacting, inter alia, with the cannabinoid and vanilloid receptors.

The compounds of the invention block this degradation pathway and increase the tissue content of these endogenous substances. They may be used in this respect in the prevention and treatment of pathologies in which the endogenous cannabinoids, and/or any other substrates metabolized by the enzyme FAAH, are involved. Examples that may be mentioned include the following diseases and complaints:

pain, especially acute or chronic pain of neurogenic type: migraine, neuropathic pain including the forms associated with the herpes virus and diabetes, acute or chronic pain associated with inflammatory diseases: arthritis, rheumatoid arthritis, osteoarthritis, spondylitis, gout, vascularitis, Crohn's disease, irritable bowel syndrome, acute or chronic peripheral pain, vertigo, vomiting, nausea, in particular post-chemotherapy nausea, eating disorders, in particular anorexia and cachexia of diverse nature, neurological and psychiatric pathologies: tremor, dyskinaesia, dystonia, spasticity, compulsive and obsessive behaviour, Tourette's syndrome, all forms of depression and anxiety of any nature or origin, mood disorders, psychoses, acute and chronic neurodegenerative diseases: Parkinson's disease, Alzheimer's disease, senile dementia, Huntington's chorea, lesions associated with cerebral ischaemia and cranial and medullary trauma, epilepsy, sleeping disorders, including sleep apnoea, cardiovascular diseases, in particular hypertension, cardiac arrhythmia, arteriosclerosis, heart attack, cardiac ischaemia, renal ischaemia, cancers: benign skin tumours, papillomas and cerebral tumours, prostate tumours, cerebral tumours (gliobastomas, medullo-epitheliomas, medullo-blastomas, neuroblastomas, tumours of embryonic origin, astrocytomas, astroblastomas, ependyomas, oligodendrogliomas, plexus tumour, neuroepitheliomas, pineal gland tumours, ependymoblastomas, malignant meningiomas, sarcomatoses, malignant melanomas, schwennomas), immune system disorders, especially autoimmune diseases: psoriasis, lupus erythematosus, connective tissue diseases, Sjögrer's syndrome, ankylosing spondylitis, undifferentiated spondylitis, Behcet's disease, haemolytic autoimmune anaemias, multiple sclerosis, amyotrophic lateral sclerosis, amylosis, graft rejection, diseases affecting the plasmocytic line, allergic diseases: immediate or delayed hypersensitivity, allergic rhinitis or allergic conjunctivitis, contact dermatitis, parasitic, viral or bacterial infectious diseases: AIDS, meningitis, inflammatory diseases, especially articular diseases: arthritis, rheumatoid arthritis, osteoarthritis, spondylitis, gout, vascularitis, Crohn's disease, irritable bowel syndrome, osteoporosis, ocular complaints: ocular hypertension, glaucoma, pulmonary complaints: respiratory pathway diseases, bronchospasms, coughing, asthma, chronic bronchitis, chronic obstruction of the respiratory pathways, emphysema, gastrointestinal diseases: irritable bowel syndrome, intestinal inflammatory disorders, ulcers, diarrhoea, urinary incontinence and inflammation of the bladder.

The use of the compounds according to the invention, in the form of the base, or a pharmaceutically acceptable acid-addition salt, hydrate or solvate, for the preparation of a medicinal product for treating the pathologies mentioned above forms an integral part of the invention.

A subject of the invention is also medicinal products comprising a compound of formula (I), or an acid-addition salt, or alternatively a pharmaceutically acceptable hydrate or solvate of the compound of formula (I). These medicinal products find their therapeutic use especially in the treatment of the pathologies mentioned above.

According to another of its aspects, the present invention relates to pharmaceutical compositions containing, as active principal, at least one compound according to the invention. These pharmaceutical compounds contain an effective dose of a compound according to the invention, or a pharmaceutically acceptable acid-addition salt, hydrate or solvate of the said compound, and optionally one or more pharmaceutically acceptable excipients.

The said excipients are chosen, according to the pharmaceutical form and the desired administration form, from the usual excipients known to those skilled in the art.

In the pharmaceutical compositions of the present invention for oral, sublingual, subcutaneous, intramuscular, intravenous, topical, local, intrathecal, intranasal, transdermal, pulmonary, ocular or rectal administration, the active principal of formula (I) above, or the possible acid-addition salt, solvate or hydrate thereof, may be administered in a unit administration form, as a mixture with standard pharmaceutical excipients, to man and animals for the prophylaxis or treatment of the above disorders or diseases.

The appropriate unit administration forms comprise oral forms such as tablets, soft or hard gel capsules, powders, granules, chewing gums and oral solutions or suspensions, sublingual, buccal, intratracheal, intraocular and intranasal administration forms, forms for administration by inhalation, subcutaneous, intramuscular or intravenous administration forms and rectal or vaginal administration forms. For topical administration, the compounds according to the invention may be used in creams, ointments or lotions.

By way of example, a unit administration form of a compound according to the invention in the form of a tablet may comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

The said unit forms are dosed to allow a daily administration of from 0.01 to 20 mg of active principal per kg of body weight, depending on the presentation form.

There may be particular cases in which higher or lower doses are suitable, and such doses also form part of the invention. According to the usual practice, the dose that is suitable for each patient is determined by the doctor according to the mode of administration and the weight and response of the said patient.

According to another of its aspects, the invention also relates to a method for treating the pathologies mentioned above, which comprises the administration of an effective dose of a compound according to the invention, a pharmaceutically acceptable acid-addition salt thereof or a solvate or hydrate of the said compound.

The invention claimed is:

1. A medicament comprising a compound of formula (I)

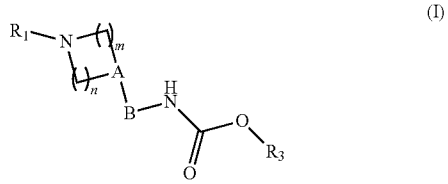

(I)

in which
A is a nitrogen atom, n is an integer equal to 2 and m is an integer equal to 2;
B is a covalent bond or a $C_{1-8}$-alkylene group;
$R_1$ is a group selected from phenyl, pyridyl, pyridazinyl, pyrimidinyl, pyrazinyl, triazinyl, oxazolyl, isoxazolyl, thiazolyl, isothiazolyl, imidazolyl, oxadiazolyl, thiadiazolyl, triazolyl, naphthyl, quinolyl, tetrahydroquinolyl, isoquinolyl, tetrahydroisoquinolyl, phthalazinyl, quinazolinyl, quinoxalinyl, naphthyridinyl, cinnolyl, imidazopyrimidinyl, thienopyrimidinyl, benzofuranyl, benzothienyl, benzimidazolyl, benzoxazolyl, benzisoxazolyl, benzothiazolyl, benzisothiazolyl, indazolyl, pyrrolopyridyl, furopyridyl, dihydrofuropyridyl, thienopyridyl, dihydrothienopyridyl, imidazopyridyl, pyrazolopyridyl, oxazolopyridyl, isoxazolopyridyl and thiazolopyridyl, said $R_1$ group being optionally substituted with one or more groups selected from R' and R";
R' is a halogen atom or a cyano, nitro, hydroxyl, $C_{1-6}$-alkyl, $C_{1-6}$-alkoxy, $C_{1-6}$-thioalkyl, $C_{1-6}$-fluoroalkyl, $C_{1-6}$-fluoroalkoxy, $C_{1-6}$-fluorothioalkyl, $C_{3-7}$-cycloalkyl, $C_{3-7}$-cycloalkyl-$C_{1-6}$-alkylene, azetidinyl, piperidyl, pyrrolidinyl, morpholinyl, piperazinyl, azepinyl, $NH_2$, $NHR_6$, $NR_6R_7$, $NR_6COR_7$, $NR_6SO_2R_7$, $COR_6$, $CO_2R_6$, $SO_2R_6$, $SO_2NR_6R_7$ or —O—($C_{1-6}$-alkylene)—O— group;

R" is a phenyl, imidazolyl, pyridyl or pyrimidinyl group;
each R" group is optionally substituted with one or more R' groups, which may be identical to or different from each other;
$R_3$ is a group of general formula $CHR_4CONHR_5$ in which:
$R_4$ is a hydrogen atom or a $C_{1-6}$-alkyl group and
$R_5$ is a hydrogen atom or a $C_{1-6}$-alkyl, $C_{3-7}$-cycloalkyl or $C_{3-7}$-cycloalkyl-$C_{1-6}$-alkylene group; and
each of $R_6$ and $R_7$ is, independently, a $C_{1-6}$-alkyl group;
or a pharmaceutically acceptable salt thereof.

2. A pharmaceutical composition containing at least one compound of formula (I) according to claim 1, in the form of a base or of a pharmaceutically acceptable acid-addition salt, and one or more pharmaceutically acceptable excipients.

3. A method of treating vomiting, nausea, and neuropathic pain, comprising administering to a patient in need thereof an effective amount of a compound of formula (I) according to claim 1, in the form of a base or of a pharmaceutically acceptable acid-addition salt.

4. A medicament comprising compound chosen from the group consisting of;

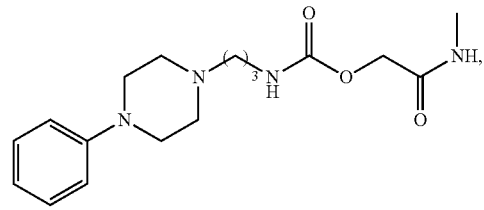

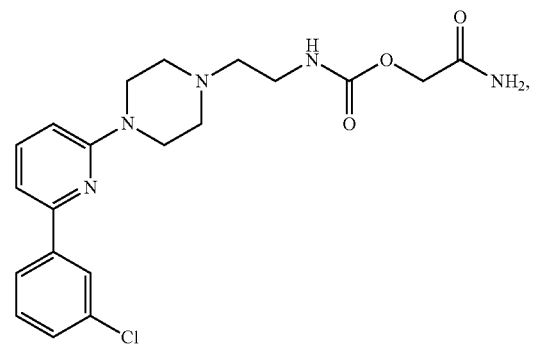

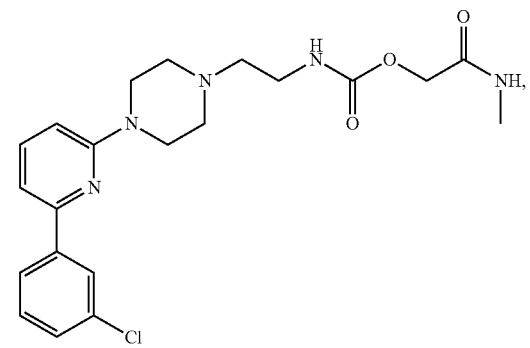

57
-continued
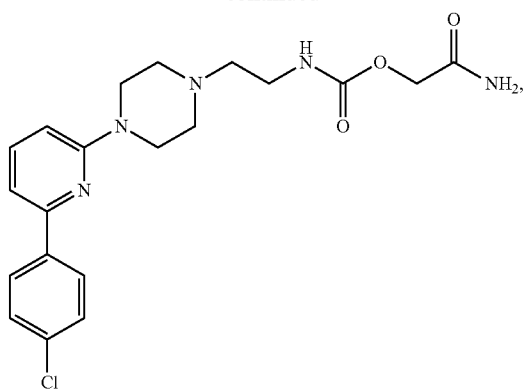
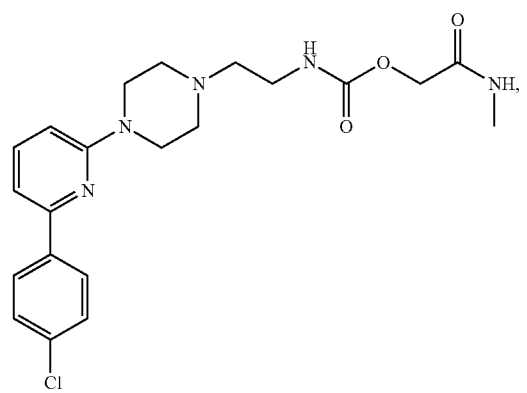
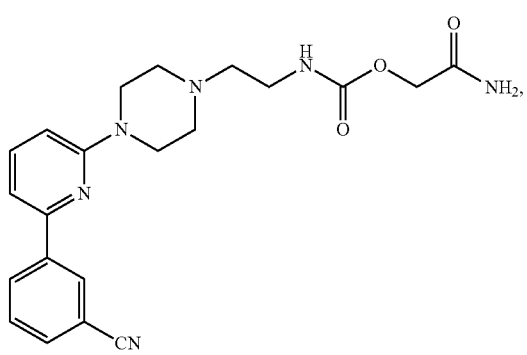
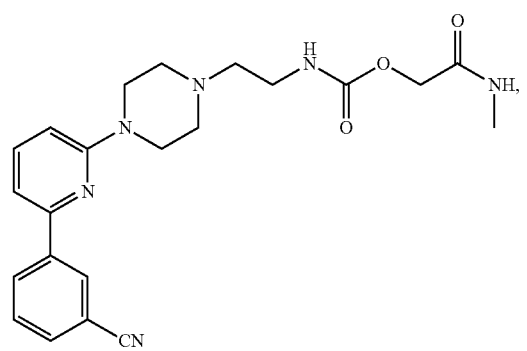
58
-continued
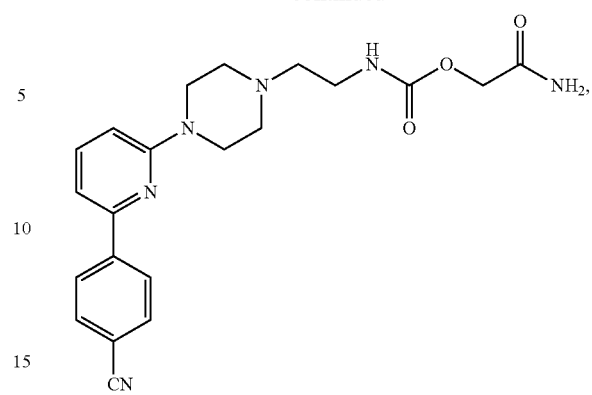
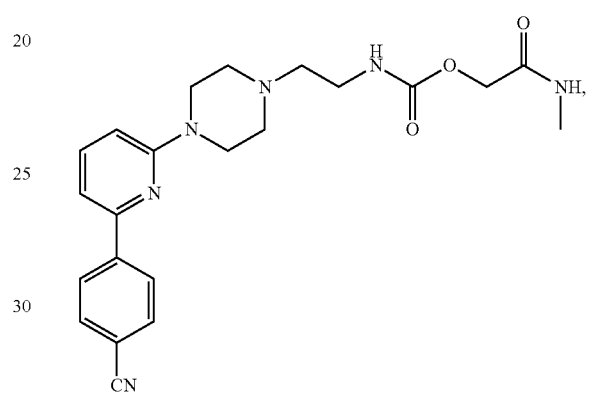
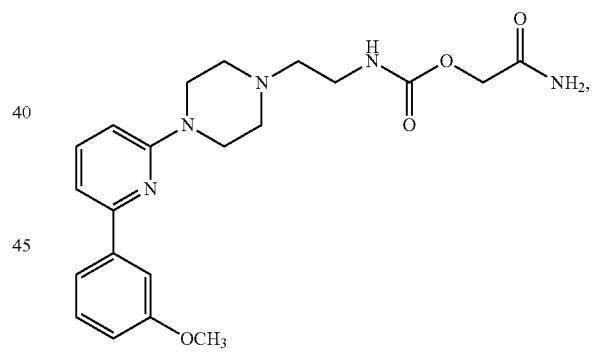
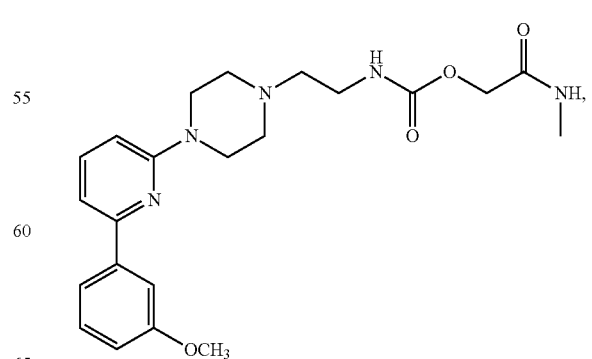

59
-continued
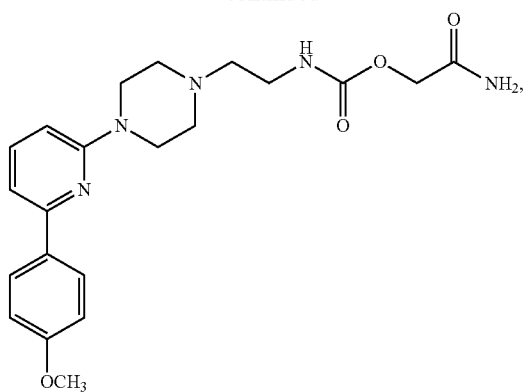
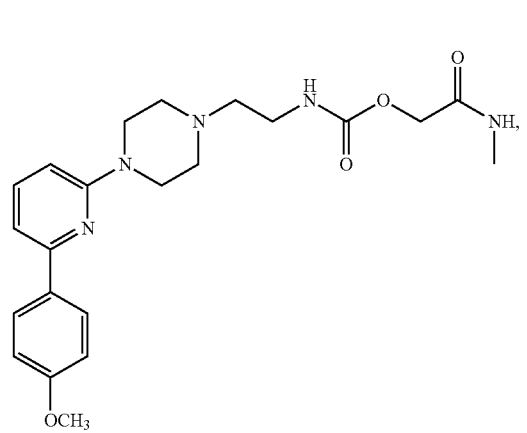
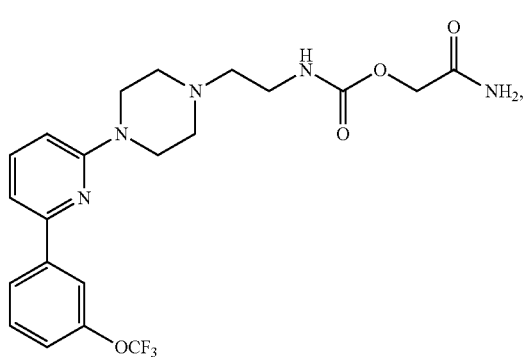
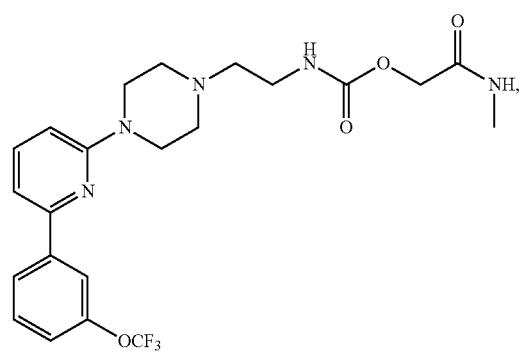
60
-continued
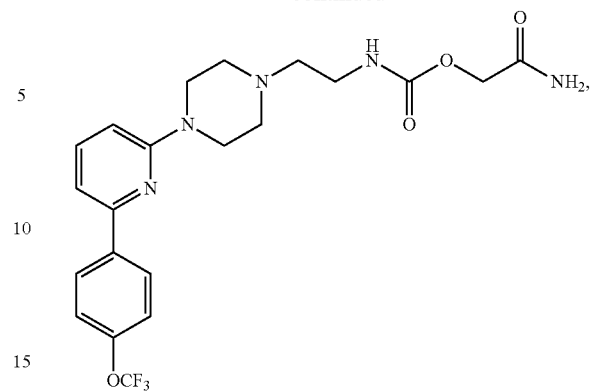
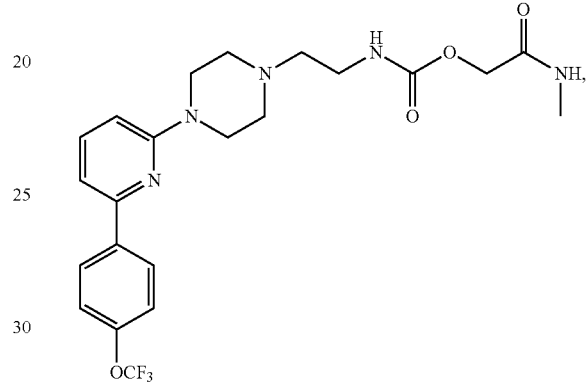
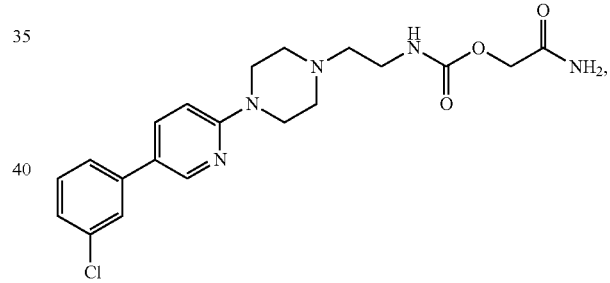
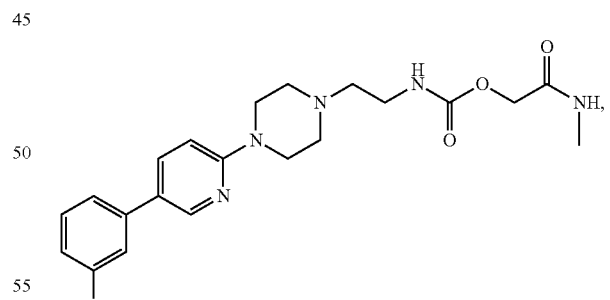
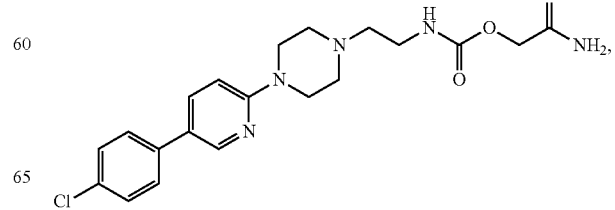

61
-continued
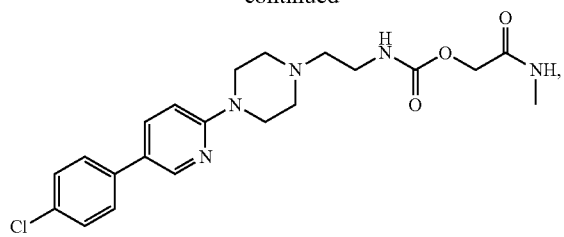
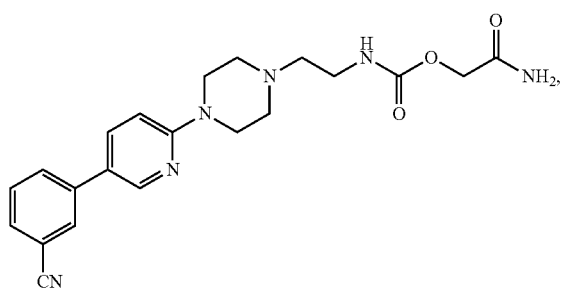
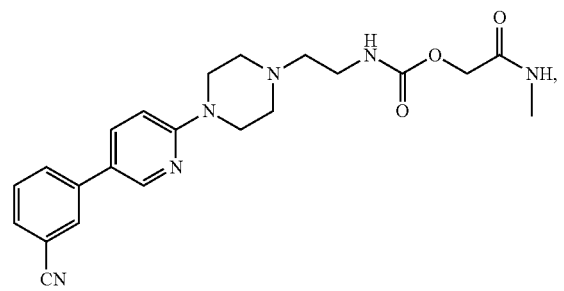
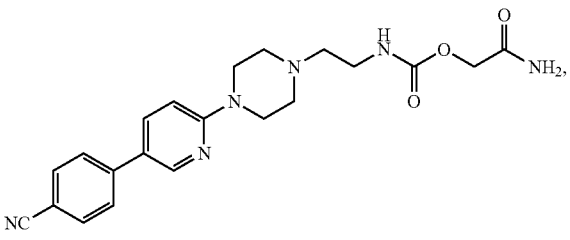
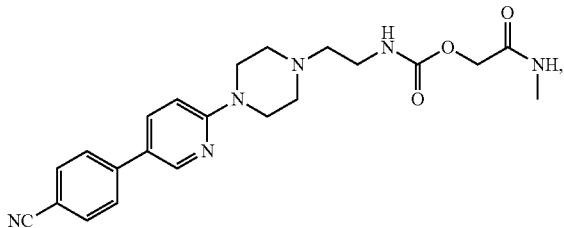
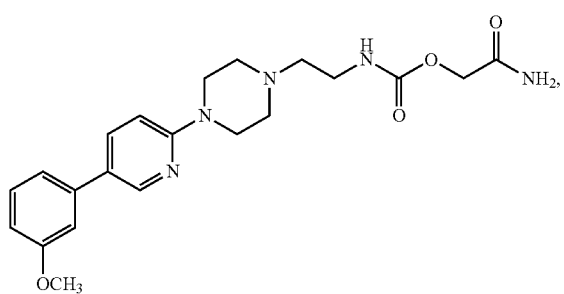
62
-continued
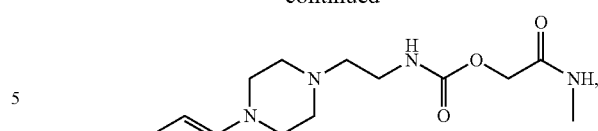
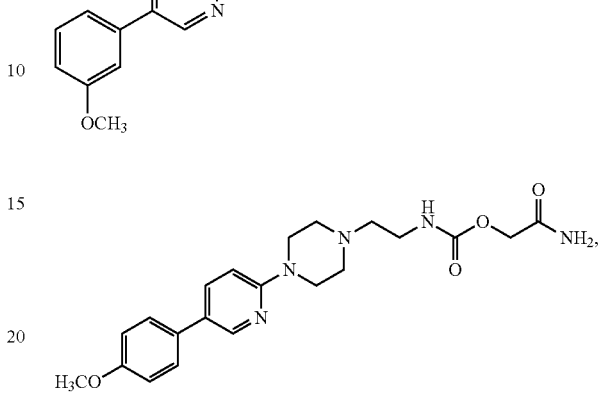
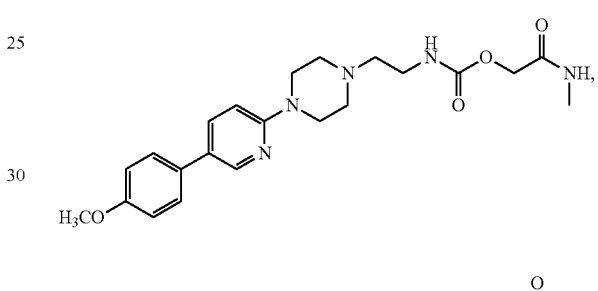
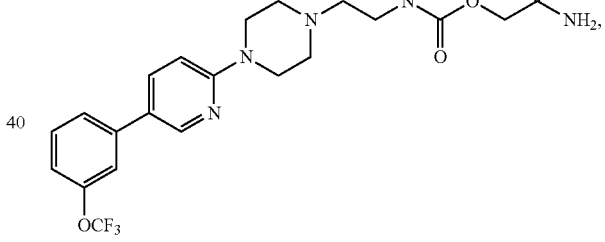
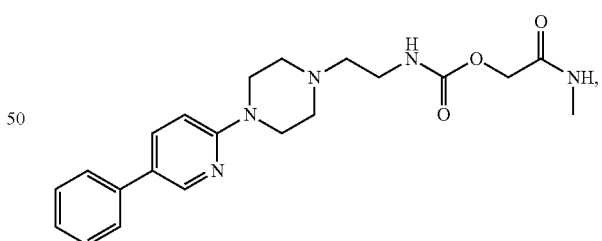
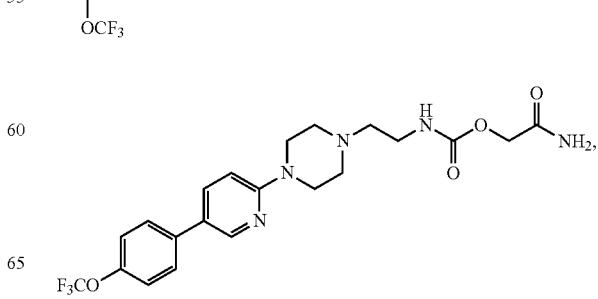

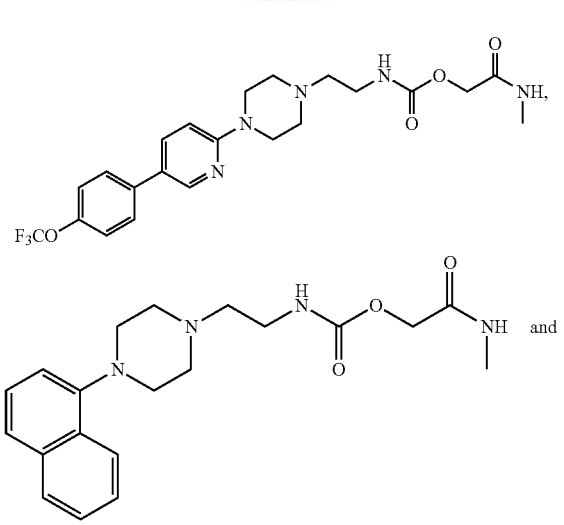

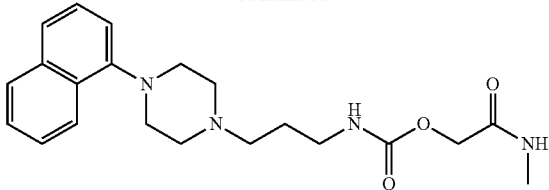

or a pharmaceutically acceptable salt thereof.

5. A pharmaceutical composition containing at least one compound according to claim 4, in the form of a base or of a pharmaceutically acceptable acid-addition salt, and one or more pharmaceutically acceptable excipients.

6. A method of treating vomiting, nausea, and neuropathic pain, comprising administering to a patient in need thereof an effective amount of a compound according to claim 4, in the form of a base or of a pharmaceutically acceptable acid-addition salt.

* * * * *